United States Patent [19]
Olney et al.

[11] Patent Number: 5,958,919
[45] Date of Patent: Sep. 28, 1999

[54] TREATMENT OF PRESYMPTOMATIC ALZHEIMER'S DISEASE TO PREVENT NEURONAL DEGENERATION

[75] Inventors: John W. Olney, Ladue; Nuri B. Farber, University City, both of Mo.

[73] Assignee: Washington University, St. Louis, Mo.

[21] Appl. No.: 08/710,727

[22] Filed: Sep. 20, 1996

[51] Int. Cl.$^6$ .................. A61K 31/40; A61K 31/445; A61K 31/495; A61K 31/55
[52] U.S. Cl. .................. 514/214; 514/249; 514/317; 514/428
[58] Field of Search .................. 514/220, 214, 514/317, 249, 428

[56] References Cited

U.S. PATENT DOCUMENTS 5,034,400  7/1991  Olney et al. ............ 514/315
5,547,963  8/1996  Poindron et al. ......... 514/317

OTHER PUBLICATIONS

Corey–Bloom, J., et al, "Adjunctive therapy in patients with Alzheimer's disease: A practical approach," *Drugs Aging* 7 : 79–87 (1995).
Gong, C.X., et al, "Inhibition of protein phosphatase–2B (calcineurin) activity towards Alzheimer abnormally phosphorylated tau by neuroleptics," *Brain Res 741*: 95–102 (1996).
Grossberg, G.T., et al, "The older patient with psychotic symptoms," *Psychiatr Serv 46*: 55–9 (1995).
Niizato, K., et al, "Long–term antipsychotic medication of schizophrenics does not promote the development of Alzheimers's disease brain pathology," *J Neurol Sci 138*: 167–7 (1996).
Rabins, P.V., "Developing treatment guidelines for Alzheimer's disease and other dementias," *J Clin Psychiatry 57 Suppl.*14: 37–38 (1996).
Schneider, L.S., "New therapeutic approaches to Alzheimer's disease," *J Clin Psychiatry 57 Suppl. 14*: 39–44 (1996).
Siegal, A., et al, "Discussion: Clinical developments in Alzheimer'disease," *J Clin Psychiatry 57 Suppl. 14* : 39–44 (1996).
Sunderland, T., "Treatment of the elderly suffering from psychosis and dementia," *J Clin Psychiatry 57 Suppl. 9*: 53–6 (1996).
Tueth, M.J., "How to manage depression and psychosis in Alzheimer's disease," *Geriatrics 50*: 43–6, 49 (1995).
Zayas, E.M., et al, "Treating the agitated Alzheimer patient," *J Clin Psychiatry 57 Suppl. 7*: 46–54 (1996).
Beal, M.F., "Does impairment of energy metabolism result in excitotoxic neuronal death in neurodegenerative illnesses?" *Ann Neurol 31*: 119–30 (1992).
Bowen, D.M., "Treatment of Alzheimer's disease. Molecular pathology versus neurotransmitter–based therapy," *Br J Psychiatry 157*: 327–30 (1990).

Cotman, C.W., et al, "Plasticity of excitatory amino acid receptors: implications for aging and Alzheimer's disease," *Prog Brain Res 86*: 55–61 (1990).
Fonnum, F., et al, "Role of glutamate and glutamate receptors in memory function and Alzheimer's disease," *Annals New York Acad Sci 757*: 475–86 (1995).
Francis, P.T., et al, "A glycine site as therapeutic target," *Annals New York Acad Sci 640* : 184–8 (1991).
Herting, R.L., "Milacemide and other drugs active at glutamate NMDA receptors as potential treatment for dementia, " *Annals New York Acad Sci 640*: 237–40 (1991).
Koh, J.Y. et al, "Beta–amyloid protein increases the vulnerability of cultured cortical neurons to excitotoxic damage," *Brain Res 533*: 315–20 (1990).
Kornhuber, J., et al, "Psychotogenicity and N–methyl–D–aspartate receptor antagonism: implications for neuroprotective pharmacotherapy," *Biol Psychiatry 41*: 135–44 (1997).
Lawlor, B.A., et al, "Does modulation of glutamatergic function represent a viable therapeutic strategy in Alzheimer's disease?" *Biol Psychiatry 31*: 337–50 (1992).
Scheuer, K., et al, "Cortical NMDA receptor properties and membrane fluidity are altered in Alzheimer'disease," *Dementia 7* : 210–4 (1996).
Ulas, J., et al, "NMDA receptor complex in the hippocampus of elderly, normal individuals and those with Alzheimer's disease," *Neuroscience 49*: 45–61 (1992).
Abramowicz, M., "Donepezil (Aricept) for Alzheimer's Disease," *The Medical Letter 39*: 53–54 (1997).
Bryson, H.M., et al, "Donepezil," *Drugs and Aging 10*: 234–241 (1997).
Ditzler, K., "Efficacy and Tolerability of Memantine in Patients with Dementia Syndrome," *Arzneim.–Forsch. /Drug Res. 41*(II) : 773–780 (1991).
Ellison, G., "The N–methyl–D–aspartate antagonists phencyclidine, ketamine and dizocilpine as both behavioral and anatomical models of the dementias," *Brain Research Reviews 20*: 250–267 (1995).
Gilman, S., "Alzheimer's Disease," *Perspectives in Biology and Medicine 40*: 230–245 (1997).
Gortelmeyer, R., et al, "Memantine in the Treatment of Mild to Moderate Dementia Syndrome," *Arzneim.–Forsch./Drug Res. 42*(II) : 904–913 (1992).

(List continued on next page.)

*Primary Examiner*—Phyllis G. Spivack
*Attorney, Agent, or Firm*—Patrick D. Kelly

[57] ABSTRACT

Methods for treating the very early (presymptomatic) stages of Alzheimer's disease are disclosed, wherein NMDA antagonist drugs are administered to protect NMDA receptors against neuronal damage. Since NMDA antagonists may cause a condition known as NMDA receptor hypofunction (NR/hypo) that triggers neurotoxic side effects, they may be co-administered with, or have inherent activity as, "safener" drugs to prevent toxic side effects. The patient's status must be monitored, so that any NMDA antagonist drugs can be discontinued if a condition of NR/hypo arises. Otherwise, the NMDA antagonist drugs can worsen and accelerate the damage caused by the disease.

6 Claims, 2 Drawing Sheets

OTHER PUBLICATIONS

Khachaturian, Z.S., "Scientific Opportuinties for Developing Treatments for Alzheimer's Disease: Proceedings of Research Planning Workshop 1," *Neurobiology of Aging 15, Suppl. 2*: S11–S15 (1994).

Marx, J., "Searching for Drugs That Combat Alzheimer's," *Science 273*: 50–53 (1996).

Mattson, M.P., "Degenerative and Protective Signaling Mechanisims in the Neurofibrillary Pathology of AD," *Neurobiology of Aging 16*: 447–457 (1995).

Olney, J.W., et al, "NMDA antagonist neurotoxicity: Mechanism and prevention," *Science 254*: 1515–1518 (1991).

Olney, J.W., et al, "Excitatory transmitter neurotoxicity and Alzheimer's disease," pp. 293–298 in *Alzheimer's Disease:Therapeutic Strategies* (Giacobini & Becker, eds., Birkhauser Publ., Boston, 1994).

Olney, J.W., et al, "NMDA receptor hypofunction, excitotoxicity, and Alzheimer's disease," *Neurobiology of Aging 16*: 459–461 (1995).

Schehr, R.S., "Therapeutic approaches to Alzheimer's disease," *Bio/Technology 12*: 140–144 (1994).

Selkoe, D.J., "Alzheimer's disease: Genotypes, phenotype, and treatments," *Science 275*: 630–631 (1997).

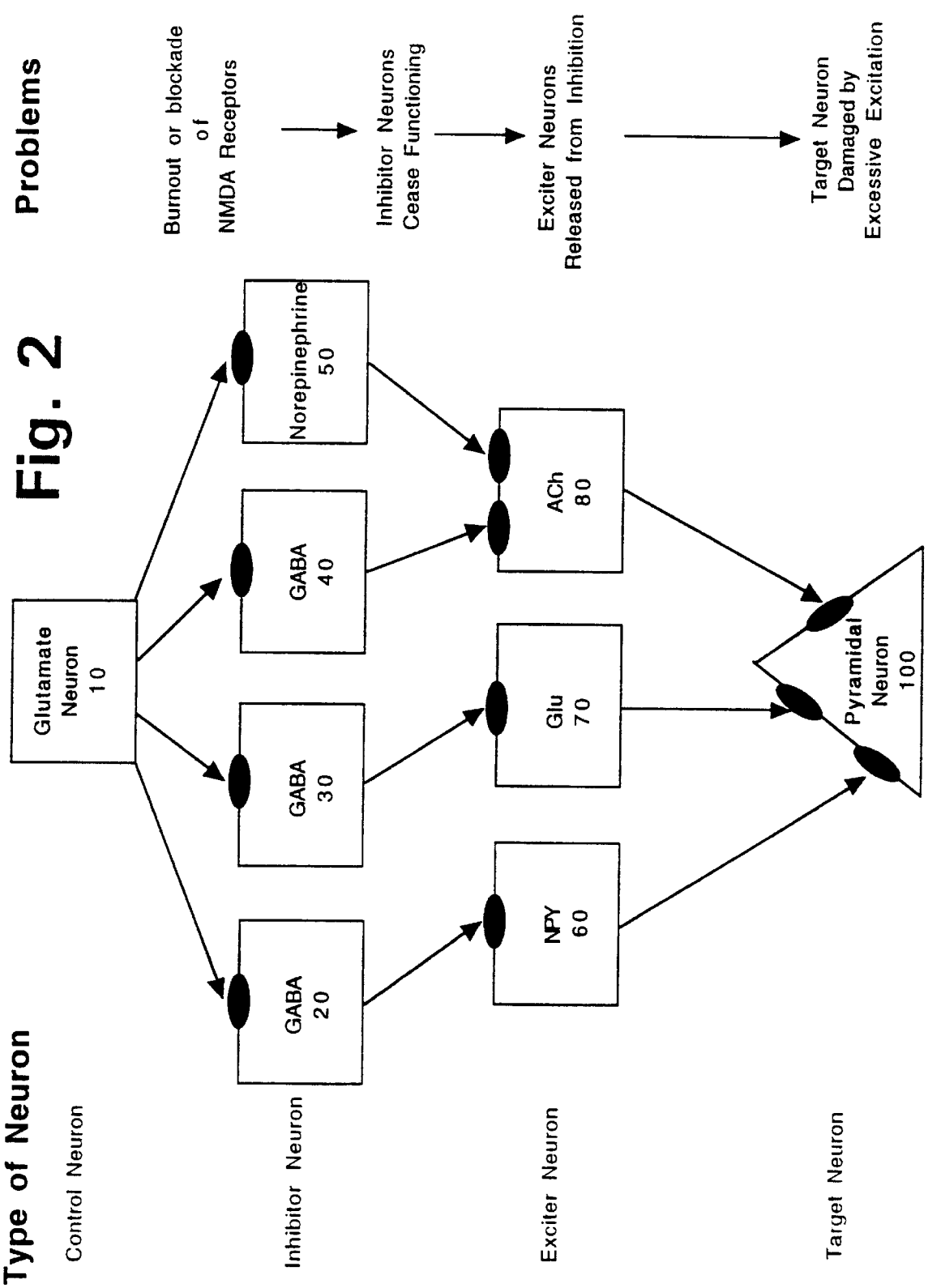

TREATMENT OF PRESYMPTOMATIC ALZHEIMER'S DISEASE TO PREVENT NEURONAL DEGENERATION

GOVERNMENT SUPPORT

The research which led to this invention was supported in part by grants from the National Institutes of Health, including grants AG 11355, DA 05072, DA 00290, and MH 38894. Accordingly, the federal government has certain rights in this invention.

BACKGROUND OF THE INVENTION

The present invention relates to neurology and pharmacology, and more specifically to drug treatments that can prevent or reduce the brain damage caused by Alzheimer's disease.

The following Background sections provide introductory information on (1) neurotransmitter receptors in the brain; (2) mechanisms by which these transmitter and receptor systems may contribute to neuronal degeneration in Alzheimer's disease; and (3) certain types of drugs that can be used to prevent or reduce neuronal degeneration in patients suffering from Alzheimer's disease.

The following Background sections are not strictly limited to prior art. The extremely complex (and apparently contradictory and paradoxical) neurological systems and processes involved in Alzheimer's disease have stubbornly confounded the efforts of literally thousands of highly skilled researchers and physicians, for decades. Accordingly, the following narrative is an effort to explain, as clearly and logically as possible, what is happening inside the brain of someone suffering from Alzheimer's disease, and how various neurological networks interact with each other in apparently paradoxical ways. Substantial parts of this explanation come from the Applicants' recent research discoveries. Because some of these recent discoveries involve neurological processes that occur naturally, inside the brain, they are discussed in the Background narrative. However, these recent discoveries by the Applicants should not be regarded as prior art.

Glutamate (GLU) and Neuronal Glutamate Receptors

Glutamate (sometimes abbreviated as GLU) is one of the 20 common amino acids used by all living cells to make protein. Glutamate is the ionized form of glutamic acid; the ionized form is the predominant form in neutral solutions, at pH 7.

In addition to its role as a building block for proteins, glutamate plays an entirely different and crucial role in the central nervous system (CNS) of higher animals, including mammals and birds. Although much of the discussion that follows is equally true for the spinal cord, which is part of the CNS, this discussion focuses on the brain, since that is where the damage and degeneration occurs in patients suffering from Alzheimer's disease.

Within the brain, glutamate serves as the predominant excitatory transmitter molecule which carries signals between nerve cells (e.g., Olney 1987; full citations to books and articles are provided below). In a brief overview, this process can be summarized as follows. At a neuronal synapse (i.e., a signal-transmitting junction between two nerve cells), a molecule of glutamate is released by the signal-transmitting neuron. The glutamate molecule enters the fluid in the gap between the two neurons, and it rapidly contacts the exposed portion of a "glutamate receptor" on the surface of the signal-receiving neuron.

As used herein, "receptor" refers to a macromolecular binding site (usually a protein, which may also be glycosylated or phosphorylated) which is at least partially exposed on the surface of a cell, and which has specific and limited affinity for one or more fluid-borne molecules, called "ligands" (these usually are neurotransmitters or hormones). When a ligand contacts an appropriate receptor, a brief binding reaction occurs which causes a cellular response, such as opening of an ion channel, which leads to activation and depolarization of the neuron. Most receptor molecules are proteins which straddle the membrane of a cell,, with an external portion for binding reactions, and an internal portion which helps carry out the cellular response that occurs when the receptor is activated by a ligand.

This is not a rigid definition, and different scientists sometimes use the term "receptor" inconsistently. For example, they may either include or exclude various additional components, such as an ion channel which is opened or closed by a receptor. All of the glutamate receptors relevant to the present invention are associated with ion channels, and therefore are referred to as "ionotropic" receptors.

In pharmacological terminology, an "agonist" is a molecule which activates a certain type of receptor. For example, glutamate molecules (and certain drugs such as NMDA, as described below) act as agonists when they excite EAA receptors. By contrast, an "antagonist" is a molecule which prevents or reduces the effects exerted by an agonist at a receptor.

Upon being activated ("excited") by a glutamate molecule, a glutamate receptor protein changes its conformation, in a manner which briefly opens an ion channel that serves as a conduit through the cell membrane. Calcium ($Ca^{++}$), sodium ($Na^+$), and certain other types of ions rapidly flow through the ion channel when it is briefly opened, thereby altering several ionic gradients that normally exist across the membranes of neurons at rest. This activates (stimulates) a neuron, causing it to release its own neurotransmitters at other ("downstream") synapses, thereby transmitting signals to still other neurons.

To reset the mechanism and get the transmitting and receiving neurons back to a resting/ready condition, where both neurons are ready to handle another nerve signal, the ion channel quickly closes, and the glutamate receptor protein on the signal-receiving neuron releases the glutamate molecule. The glutamate molecule floats back into the synaptic fluid between the neurons, and a molecular transport system quickly intercepts it and transports it back inside the transmitting neuron. The signal-receiving neuron activates a set of molecular pumps, which rapidly transport calcium and sodium ions (which had entered the cell though the glutamate-controlled ion channel) back out of the neuron to regain a "polarized" condition, so that it will be ready to receive another nerve signal.

This entire set of chemical actions—release of glutamate by a transmitting neuron, activation and depolarization of a signal-receiving neuron, release of the glutamate transmitter molecule by the receptor protein, clearance of the free glutamate from the synaptic fluid, and restoration of the polarized/ready state in the signal-receiving neuron—is extraordinarily rapid. All of these steps, together, occur within a few milliseconds.

Since glutamate is an amino acid that can function as an excitatory neurotransmitter inside the brain, it is often called an "excitatory amino acid" (EAA). Another type of amino acid, aspartate (the ionized form of aspartic acid), can also function as an excitatory amino acid in the brain; therefore, glutamate receptors are sometimes referred to as "EAA" receptors, since they can be triggered by either of two amino acids (glutamate or aspartate). However, glutamate is used much more widely than aspartate as a neurotransmitter, and "EAA receptors" are referred to herein (and by most scientists) as glutamate or GLU receptors.

Types of GLU Receptors: NMDA and non-NMDA Receptors

There are three distinct types of ionotropic glutamate receptors in the mammalian central nervous system (as well as a "metabotropic" glutamate receptor, which is not of interest herein). Although all three GLU receptor types are normally triggered by exactly the same EAA neurotransmitters in the CNS (i.e., glutamate or aspartate molecules), these three different subtypes of glutamate receptors have been found by researchers to have different binding properties, when certain types of artificial drugs are used as probes to study neuronal activity.

One major class of GLU receptors is referred to as NMDA receptors, since they bind preferentially to NMDA, which is n-methyl-D-aspartate. This analog of aspartic acid normally does not occur in nature, and is not present in the brain; it is, however, a useful probe drug which is widely used by neurologists to study and differentiate the roles of NMDA and non-NMDA receptors. When molecules of NMDA contact neurons having NMDA receptors, the NMDA strongly activates NMDA receptors, and acts as a glutamate agonist, causing the same type of neuronal excitation that glutamate causes.

The second class of glutamate receptors is called "kainic acid" (KA) receptors, since they are activated by kainic acid, another artificial drug that does not normally occur inside the brain.

The third class of GLU receptors is referred to herein as AMPA receptors; they are activated by both quisqualic acid (and its ionized form, quisqualate) and by alpha-amino-3-hydroxy-5-methyl-4-isoxazole (abbreviated as AMPA). Until the mid-to-late 1980's, AMPA receptors were called quisqualate (QUIS) receptors; however, quisqualate also activates a different type of receptor called a metabotropic receptor, so the recent trend is to call QUIS-type EAA receptors by the name "AMPA" receptors.

KA receptors and AMPA receptors are more closely related to each other (both structurally, and by higher levels of cross-affinity to various drugs) than to NMDA receptors. In addition, they could not be distinguished from each other for several years after it was recognized that there were NMDA-affinity receptors as well as other classes of glutamate receptors. For both of these reasons (scientific, and historical), KA and AMPA receptors are often referred to collectively as "non-NMDA" receptors.

The NMDA receptor complex (which includes an ion channel) has a number of distinct binding sites (also called recognition sites), where several different substances can bind to and modify the ion-channel-opening actions of glutamate. Thus, there are several different types of NMDA antagonists; each type is characterized in terms of the binding site with which it interacts.

"Competitive" NMDA antagonists compete with glutamate at the glutamate binding site (which is also the NMDA binding site). The action of glutamate at this site promotes opening of the ion channel to allow $Na^+$ and $Ca^{++}$ ions to flow into the cell. Competitive antagonists block the action of glutamate at this site, and prevent opening of the ion channel; thus, they are often referred to as "closed channel blockers." Competitive NMDA antagonists being developed by drug companies are usually given acronyms or code numbers; these include, but are not limited to, compounds such as CPP (Boast 1988), D-CPP-ene (Herrling 1994), CGP 40116 (Fagg et al 1989), CGP 37849 (Fagg et al 1989), CGS 19755 (Boast 1988 and Grotta 1995), NPC 12626 (Ferkany et al 1989), and NPC 17742 (Ferkany et al 1993). Other competitive NMDA antagonists include D-AP5 (D-2-amino-5-phosphonopentanoic acid), D-AP7, CGP 39551 (D,L(E)-2-amino-4-methyl-5-phosphono-3-pentenoic acid carboxyethyl ester), CGP-43487, MDL-100, 452, LY-274614, LY-233536, and LY-233053.

Regrettably, even though these drugs held early promise for possibly reducing brain damage caused by stroke, cardiac arrest, etc., most of these drugs have been shown to cause pathological changes in certain regions of the mammalian brain, in lab animals (Olney et al 1991; Hargreaves et al 1993). All of these drugs that have been tested in adult humans have also been shown to cause psychotomimetic reactions, such as hallucinations, which suggest that similar types of damage in certain vulnerable regions of the brain may also occur in humans when competitive NMDA antagonists are administered (Grotta 1995; Herrling 1994; Kristensen et al 1992).

There are also other sites in the NMDA receptor complex, located outside the ion channel, where glycine or certain types of polyamines can bind. Binding of glycine and polyamines to these sites exerts a cooperative action that assists glutamate in opening the ion channel. Accordingly, it is hoped and believed by some that drugs which block the glycine or polyamine sites may have neuroprotective actions which are comparable to, but somewhat milder than, competitive antagonists which act at the glutamate binding site. Glycine and polyamine site antagonists include but are not limited to kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, ACEA 1021, ACES 1031, arcaine, diethylenetriamine, 1,10-diaminodecane, 1,12-diaminododecane, ifenprodil, and SL-82.0715. For reviews and citations, see Carter et al 1988, Rogawski 1992, Massieu et al 1993, Keana et al 1995, and Warner et al 1995.

Within the NMDA receptor ion channel, there is a site where phencyclidine (PCP) and several other drugs (including dizocilpine, ketamine, tiletamine, and CNS 1102) bind selectively. When these agents bind to the PCP site in the ion channel, they block ion flow through the channel, even if the channel otherwise remains open: thus, drugs that block activity at NMDA receptors by binding to the PCP site are sometimes referred to as "open channel blockers".

Dizocilpine is the most selective and effective non-competitive NMDA antagonist ever discovered; it is powerful and highly selective at the PCP binding site. The full chemical name is (+)-5-methyl-10,11-dihydro-5H-di[a,d] cyclohepten-5,10-imine. The maleate salt of dizocilpine is commercially available to researchers under the name MK-801, and MK-801 has been investigated extensively for use as an antiepileptic and for preventing damage due to cerebral ischemia. However, it has been shown, even at relatively low doses, to produce pathological changes in cerebrocortical neurons in adult rats (Olney et al 1989).

Phencyclidine is a dissociative anesthetic, formerly used in human and veterinary medicine, that is illicitly abused as a hallucinogenic drug under the street name "angel dust". This drug can induce a psychosis which is clinically indistinguishable from schizophrenia, and it has been shown at relatively low doses to produce pathological changes in various corticolimbic regions of the adult rat brain (Olney et al 1989, Corso et al 1994).

Ketamine is a dissociative anesthetic that is currently being used in human anesthesia, and is the only NMDA antagonist that is currently being used for anesthetic purposes. It is suitable for human anesthesia because it has an exceedingly short duration of action (usually about 15 minutes), which assures that its effects on the CNS, including adverse CNS effects, can be rapidly reversed by termination of ketamine administration. Despite its short duration of action, it occasionally produces an "emergence" reaction during recovery from anesthesia that is characterized by unpleasant dreams, confusion, agitation, hallucinations, and irrational behavior. Ketamine has recently been studied for its psychotomimetic effects and has been described as an agent that produces symptoms in normal humans that are indistinguishable from the symptoms of psychosis and thought disorder seen in schizophrenia (Krystal et al 1994). Ketamine also has been shown to cause pathological changes in the cerebral cortex of adult rats (Olney et al 1989).

Tiletamine, also used in veterinary medicine as an anesthetic, is another non-competitive NMDA antagonist which acts at the PCP binding site. It has also been shown to cause pathological changes in the cerebral cortex of adult rats (Olney et al 1989).

Toxic Effects of Excessive NMDA Receptor Activity; Use of NMDA Antagonists to Reduce Excitotoxic Damage Excessive activation of NMDA receptors by endogenous glutamate is thought to play a major role in a number of important CNS disorders. In an acute crisis such as a stroke or CNS trauma, and in certain other events such as severe epileptic seizures, the cellular transport mechanism that removes glutamate almost immediately from the synaptic fluid, and pumps it back inside a neuron for subsequent re-use, can run out of energy to drive the glutamate clearance process. If this occurs, excessive glutamate begins to accumulate in the synaptic fluid between neurons. If glutamate molecules are not being removed from synapses at adequate rates, they begin to repeatedly and persistently excite glutamate receptors on signal-receiving neurons. This drives the receptor-bearing neurons into a state of hyper-excitation which can kill the neurons, through a process called "excitotoxicity" (e.g., Olney 1990, Choi 1988, Choi 1992).

Excessive activity at NMDA receptors can also severely aggravate neuronal damage caused by trauma (mechanical injury) to the brain or spinal cord. Many trauma victims suffer from a dangerous and potentially lethal increase in intracranial pressure, which involves water flowing into neurons in an effort to sustain osmotic balance as charged ions flow into the neurons during neuronal excitation. Elevated intracranial pressure is a major cause of morbidity and mortality in CNS trauma victims, and NMDA antagonists are potentially useful in reducing intracranial pressure following such crises.

As used herein, the term "acute insult to the central nervous system" includes short-term events which involve or pose a threat of neuronal damage mediated by glutamate excitotoxicity. This includes ischemic events (which involve inadequate blood flow, such as a stroke or cardiac arrest), hypoxic events (involving inadequate oxygen supply, such as drowning, suffocation, or carbon monoxide poisoning), trauma in the form of mechanical or similar injury, certain types of food poisoning which involve an excitotoxic poison such as domoic acid, and seizure-mediated neuronal degeneration, which includes several types of severe epileptic seizures. NMDA antagonists can help to protect neurons in the CNS against such damage (e.g., Olney 1990; Choi 1992). Accordingly, a number of NMDA antagonists (i.e., drugs that can suppress glutamate's excitatory activity at NMDA receptors) are being studied by several major pharmaceutical companies.

Despite the intense interest and research in NMDA antagonist drugs, for roughly a decade now, no NMDA antagonists have been approved for human use, except in very limited clinical trials (this excludes ketamine, which was approved for use as a short-acting anesthetic, during surgery, before the toxic side effects of NMDA antagonists were recognized). Presumably, this is because of the toxic side effects that these drugs cause in certain regions of the brain.

Various types of "safener" agents have been known for years, which can prevent those toxic side effects (see, e.g., Olney 1991, and U.S. Pat. No. 5,034,400 (Olney 1991)). However, except possibly in small clinical trials, NMDA antagonists still are not being used on humans, despite the current knowledge about safener agents.

In addition to neuronal damage caused by acute insults, excessive activation of glutamate receptors may also contribute to more gradual neurodegenerative processes leading to cell death in certain chronic neurodegenerative diseases, including amyotrophic lateral sclerosis (Lou Gehrig's disease), Parkinson's disease and Huntington's chorea (Olney 1990). It is considered likely, by many researchers in this field, that NMDA antagonists may someday prove useful in the therapeutic management of such chronic diseases.

As noted below, several neurological researchers (including the Applicants) have proposed that excessive activation of NMDA receptors may also play a role in Alzheimer's disease, a neurodegenerative disease that is discussed in some detail below. However, it now appears (based on recent discoveries by the Applicants, as disclosed herein) that in the very early stages of Alzheimer's disease, there is a shift from one form of NMDA receptor dysfunction, to an entirely different form of NMDA receptor dysfunction. This will be explained below.

NR/Hypo as a Drug-Induced Phenomenon: Both Beneficial and Detrimental

A condition of NMDA receptor hypofunction (NR/hypo) can be created, inside the brains of laboratory animals, by administering an NMDA antagonist drug (i.e., a drug which blocks or reduces activity at NMDA receptors). When NR/hypo is deliberately created, using NMDA antagonist drugs, it can have important beneficial effects in protecting brain tissue against acute excitotoxic damage due to a crisis such as a stroke, cardiac arrest, or brain trauma. Therefore, pharmaceutical companies have devoted hundreds of millions of dollars to research funding, in an effort to develop safe NMDA antagonist drugs that can be used to treat people suffering from such crises.

However, despite their potential benefits, NMDA antagonists have serious detrimental side effects. As described in Olney et al 1989b and in U.S. Pat. No. 5,034,400 (Olney 1991), they can injure and even kill neurons located in a portion of the brain known as the posterior cingulate or retrosplenial (PC/RS) cortex, and in certain other cerebrocortical and limbic regions of the animal brain.

These toxic side effects, caused by NMDA antagonists, can be evaluated and measured directly, in brain tissue from lab animals that have been sacrificed. Such tests are most commonly done on rats. Briefly, in sacrificed animals which have been administered an NMDA antagonist drug (such as MK-801) without an accompanying safener drug, several pathological changes become fairly obvious and easily detectable in neurons located in the PC/RS cortex region of the brain. Such changes include (1) the formation of vacuoles (i.e., small bag-like sacks or organelles which are empty of the type of cellular structures that normally fill other organelles inside a cell cytoplasm; (2) mitochondrial damage or dissolution; and (3) the induction and expression of so-called "heat shock" proteins. All three of these measurable indicators (vacuole formation, mitochondrial damage, and expression of heat shock proteins) can be regarded as manifestations of serious damage to affected cells, indicating major disruption or derangement of a cell's normal structure and functioning. These cellular changes can also be correlated with behavioral abnormalities in lab animals, such as seizures, catatonic withdrawal, and abnormal responses to conventional stimuli.

In living human patients, since direct examination of brain tissue is usually not feasible prior to death, the appearance of hallucinations or other psychotomimetic symptoms (such as severe disorientation or incoherence) is regarded as a warning sign that similar types of neuronal damage may be occurring in the human brain, when NMDA antagonists are used.

Thus, a major obstacle to the use of NMDA antagonists as therapeutic drugs in humans lies in their potential for inducing toxic side effects inside the brain, including neuronal damage and even neuronal death, in certain vulnerable regions of the brain.

Safener Drugs for Preventing Toxic Side Effects of NMDA Antagonists

It has been discovered, largely by the Applicants herein, that several types of drugs can act as "safener" agents to reduce or prevent the toxic side effects caused by NMDA antagonists. Safener drugs that have previously been described are listed below. Not all of these drugs are suitable for long-term administration; however, this brief listing is provided for completeness.

(1) Anticholinergic drugs which block the muscarinic class of cholinergic receptors. These are described in more detail in Olney et al 1991, and in U.S. Pat. No. 5,034,400 (Olney 1991).

(2) Benzodiazepine drugs which can increase ("potentiate") the effects of a naturally-occurring inhibitory neurotransmitter called gamma-amino-butyric acid (GABA) have some efficacy in preventing toxic side effects of NMDA antagonists. However, even in very high dosages, these drugs are not completely effective. They can only act to enhance the effects of naturally-occurring GABA, and they become ineffective when inadequate supplies of naturally-occurring GABA are not present. Examples include diazepam, which is sold under the trademark VALIUM, and its various analogs.

(3) Other drugs which can act directly at GABA type A ($GABA_A$) receptors, to open the chloride ion channel even in the absence of naturally occurring GABA, can block the toxic side effects of NMDA antagonists much more effectively than benzodiazepine drugs (see U.S. Pat. No. 5,474,990, Olney 1995). This class of drugs, called "direct GABA agonists", includes certain barbiturates such as secobarbital and pentobarbital. It also includes certain anesthetics such as isoflurane and halothane, which are administered by inhalation, as well as propofol, an intravenous anesthetic.

(4) Drugs that can bind to a class of receptors called sigma receptors, as described in Farber et al 1993. These drugs include di(2-tolyl)guanidine and rimcazole, which are relatively selective for sigma receptors, as well as other drugs such as haloperidol, thioridazine and loxapine, which interact with dopamine receptors as well as sigma receptors.

(5) Drugs that act as agonists at a class of receptors called alpha-2 adrenergic receptors. Drugs in this class include clonidine, p-iodoclonidine, guanabenz, guanfacine, xylazine, and lofexidine (Farber et al 1995a and 1995b).

(6) Certain types of antipsychotic agents, including clozapine (Farber et al 1993), olanzapine, and fluperlapine (Farber et al 1996). In addition to acting at dopamine, serotonin, and norepinephrine receptors, these drugs also bind to and suppress activity at muscarinic receptors. Accordingly, these drugs can be grouped together with the anti-cholinergic (muscarinic antagonist) drugs mentioned in item #1, above.

In addition to the foregoing classes of drugs, which have been publicly identified as being capable of blocking the toxic side effects of NMDA antagonists, the Applicants' recent research has also identified certain additional types of drugs that can accomplish that same goal, but which have not previously been publicly disclosed as having that capability. These additional classes of drugs are identified and discussed below, following the Summary of the Invention.

Before proceeding further, another phenomenon needs to be analyzed, involving inhibitory neurotransmitter receptor systems and a potentially pathological process known as "disinhibition".

Inhibitory/Excitatory Transmitter Interactions; Disinhibition

It was mentioned above that in the brain, glutamate is the principle type of excitatory neurotransmitter. Several other types of neurotransmitters also need to be discussed, since the interactions between glutamate and these systems are important to this invention.

Another major excitatory neurotransmitter is acetylcholine (abbreviated as ACh). Like glutamate receptors, there are several different types of ACh receptors on neurons in the brain. These are generally divided into "muscarinic" and "nicotinic" classes of ACh receptors. The muscarinic class is further subdivided into m1, m2, m3, m4, and m5 subclasses.

When a molecule of ACh contacts an ACh receptor on a neuron, this triggers a signal transduction process involving certain "second messenger" systems within the neuron, the net result being that a higher state of electrical activity is induced; this is another way of saying that the neuron is excited by ACh. In addition, at some muscarinic receptors, especially m2 receptors, ACh may have predominantly inhibitory or autoregulatory effects, instead of excitatory effects.

In the mammalian brain, there also is a type of neurotransmitter receptor system referred to as the "sigma" receptor system. Although this system has been known for many years, progress has been slow in identifying the endogenous transmitter molecule that activates this system. Recent evidence indicates that a certain peptide molecule that is abundantly contained in certain CNS neurons, called neuropeptide Y (NPY), has an important role in modulating the IV function of sigma receptors. The effects of NEIY on the sigma receptor system appear to be mainly excitatory.

Accordingly, in the brain circuitry that is relevant to the present invention, there are three excitatory transmitter receptor systems (glutamate, ACh, and sigma) and three corresponding excitatory transmitter molecules (glutamate, ACh and NPY, respectively).

In addition to these three excitatory transmitter systems, there are also transmitter systems in the CNS that are primarily, or in some cases exclusively, inhibitory. These inhibitory systems are absolutely essential to proper functioning of the brain. In a simplified summary, they can be regarded as serving two distinct functions. First, they help a neuron quickly restore itself to a "resting/ready" condition, so that it will be ready to receive the next nerve signal from other neurons. And second, they help suppress or "tune out" activity caused by unwanted impulses. This is analogous to a TV or radio receiver, which cannot function properly unless it can be tuned to a single channel or station, so that it suppresses and ignores the competing signals from dozens or hundreds of other transmitting stations that may be broadcasting in the area.

Another way to understand both the importance and the mechanism of inhibitory neurotransmitters and receptors is to think in terms of gatekeepers, which establish threshold values. If a weak, low-level signal that does not reach a necessary threshold strength tries to activate a neuron, the gatekeeper will block it. However, if an incoming signal or stimulus reaches or surpasses the threshold level, the gatekeeper will let it through. It will then trigger what is, in effect, an on/off switch which controls the activation, firing, and depolarization of the neuron. This inhibitory/gatekeeping function is essential for reducing spurious and unwanted nerve cell activations in the brain, so that coherent, meaningful patterns of signals (stimuli, thoughts, memories, etc.) can be handled properly and effectively by the brain.

The predominant inhibitory transmitter in the brain is GABA (the acronym for gamma-amino butyric acid). This inhibitory transmitter has important interactions with the glutamate excitatory system in many neural circuits within the CNS. Neurons that contain and release GABA as an inhibitory transmitter are called GABAergic neurons.

As is discussed in more detail below, there is phenomenon involving the GABA system known as "disinhibition" which can play an important role in neuropathological disease processes. The GABA system normally is constantly active in maintaining a certain level of inhibitory tone which exerts a restraining influence on the major excitatory pathways (including both glutamatergic and cholinergic systems) in the brain. The GABA system maintains a state of constant inhibitory activity by virtue of being steadily driven by glutamate. This glutamate is released by neurons at synapses which use NMDA receptors on the "incoming" or "upstream" surfaces of the GABA-releasing neurons. Thus, paradoxically, glutamate is the driving force behind a multi-component inhibitory system that functions to restrain glutamate and other excitatory systems so that they will not over-excite and damage other neurons in the brain. This system is discussed in more detail below, and is schematically depicted in FIGS. 1 and 2.

It follows, if brain systems are organized in this manner, that if the NMDA receptors on the GABA-releasing neurons, through which glutamate drives the inhibitory restraining system, are impaired or destroyed (i.e., if an NR/hypo condition is created inside the brain), the restraining action will be abolished and the excitatory systems that were being restrained will be released from inhibition ("disinhibited"). Unrestrained excitatory activity will then serve as a pathological mechanism that can cause neuronal degeneration in the brain circuits that have been disinhibited.

NR/Hypo as a Disease Mechanism

Before analyzing the correlations between NR/hypo and Alzheimer's disease, it should be noted that there has been some interest in NR/hypo as a disease process, but this interest has been focused upon schizophrenia and not Alzheimer's disease. These two diseases are so totally different, in their symptoms and manifestations, that various published suggestions that NR/hypo is involved in schizophrenia (e.g., Olney and Farber 1995) would be regarded, by most neurologists, as teaching away from possible involvement as a causative mechanism in Alzheimer's disease. This may be one of the reasons that (apparently) no other neurological researchers have noticed any correlations between NR/hypo and Alzheimer's disease.

Schizophrenia is not of interest herein; this current invention solely involves the treatment and prevention of Alzheimer's disease. To the best of the Applicants' knowledge and belief, no one else has ever suggested that NR/hypo might be a causative mechanism in Alzheimer's disease.

Alzheimer's disease

Alzheimer's disease is a progressive neurodegenerative disorder which mainly affects people over the age of 60. Memory loss and general cognitive deterioration, often leading to disorientation, extreme forgetfulness, and an inability to care for one's self or one's affairs, are the primary symptoms; however, these terms are inadequate to convey the mental devastation, family suffering, and economic and social costs that the disease inflicts on its victims and their families when elderly parents can no longer function, travel in society, or (in many cases) even recognize their own children.

The disease does not immediately become clear and apparent in its early stages, and only becomes evident over a prolonged span of time, which may cover years. This is especially true since nearly everyone suffers from some level of memory loss as they age into their sixties and seventies, and this type of normal memory loss can mask the early onset and recognition of Alzheimer's disease. Therefore, it is impossible to accurately determine how many people suffer from Alzheimer's disease. However, it has been estimated that tens of millions of elderly people suffer from Alzheimer's disease at some level, and the numbers continue to grow as advances in other areas of health care prolong life expectancies and allow Alzheimer's disease to manifest itself more frequently. There can be no doubt that Alzheimer's disease is one of the most important and costly health problems, among the elderly.

Neuropathological damage which can be measured in the brain after death include atrophy (shrinkage, loss of mass, and loss of healthy, viable tissue) in the forebrain, massive loss of neurons and synaptic complexes, and the presence in many brain regions of neurofibrillary tangles and amyloid plaques. Interestingly, the amyloid plaques have a different distribution than the neurofibrillary tangles; however, no one previously has offered a satisfactory explanation for those distributions.

Various diagnostic tests and analyses have been developed for diagnosing Alzheimer's disease. These tests can be divided into three major categories: genetic analysis, cognitive testing, and brain scans.

The first category, genetic analysis, involves biochemical analysis of genes from cells (e.g., blood cells) taken from a patient or suspected patient. Certain isoforms (or alleles) of certain genes are known to substantially increase the risk that a person carrying that gene will manifest the symptoms of Alzheimer's disease; an unfavorable isoform may also be associated with an earlier onset of symptoms. In addition, genetic mutations that invariably cause Alzheimer-type dementia to occur within certain families, usually with early onset, have been discovered. Genetic analysis is discussed in more detail below.

The second major category involves cognitive testing, in which the patient responds to questions which evaluate perception, memory, and analytical abilities. Various such tests, which are sufficiently sophisticated to be able to detect the earliest outward manifestations of Alzheimer's disease, are described in articles such as Morris 1993, and Morris et al 1988.

The third major category involves neuro-imaging (also called brain scans). The major type that was first developed, called CAT scans (CAT is the acronym for computerized axial tomography), has been superseded by magnetic resonance imaging (MRI), which provides better and clearer pictures with finer resolution. Both of these scanning types reveal structural details inside the brain; they do not require administration of special drugs to the patient, and they only reveal static structures, rather than areas where neuronal activity is occurring.

Two other types of scans can analyze brain activity, rather than merely static structures. PET scanning (PET stands for positron emission tomography) involves administration of special drugs that are usually labelled with short-lived radioactive isotopes. These drugs create highlighted areas in a scan, and the highlighted areas indicate areas of increased neuronal receptor binding or neuronal activity, inside the brain. A more recent and improved approach is called magnetic resonance spectroscopy; like PET scans, it involves administration of special drugs to a patient, and these drugs highlight areas of elevated binding or activity in the brain.

There are many published reports indicating that various abnormalities in the brains of Alzheimer patients (including very early stage Alzheimer patients) can be detected via brain scans. Review articles which summarize and cite such reports include Jagust 1996, Rossor et al 1996, and Smith 1996.

In summary, an enormous amount of research effort and funding has been spent on Alzheimer's disease, and a number of sophisticated diagnostic methods have been developed. Cognitive testing methods can diagnose Alzheimer's disease in its very earliest clinical stages, and by genetic analysis and neuro-imaging performed prior to onset of symptoms, it is often possible to identify individuals who are at increased risk of developing Alzheimer's disease, and in some cases to predict with certainty that specific individuals are destined to be afflicted with the disorder.

Despite extensive research, which has been continuing for decades, no one has previously managed to clearly decipher the etiologic mechanisms of Alzheimer's disease. In addition, with a single very limited exception (which involves a drug called tacrine, which provides only a brief and equivocal respite from the onslaught of Alzheimer's disease, as discussed below), no one has previously been able to specify any drug treatment which can actually reduce, retard, or prevent the ongoing neurological devastation caused by Alzheimer's disease. As discussed below, all other treatments are merely palliative, i.e., they merely try to make an Alzheimer's patient more comfortable while the damage continues inside his or her brain.

Prior to this invention, the two most prominent schools of thought regarding the neurodegenerative changes in Alzheimer's disease have involved genetics, and excitotoxicity. The positions maintained by these two differing schools of thought can be briefly summarized as follows.

Genetics School

As noted above, geneticists have identified several specific genetic factors which they believe may be of etiological significance in Alzheimer's disease. The two types of genes that are of greatest interest in Alzheimer research are: (1) genes which encode a protein known as apolipoprotein-E; and (2) genes that encode amyloid precursor proteins which, when enzymatically cleaved, give rise to beta amyloid, a protein that is an important ingredient of amyloid plaques.

Review articles which survey studies involving apolipoprotein-E include Schellenberg 1995, Mayeux and Schupf 1995, and the "Statement on use of apolipoprotein E testing for Alzheimer disease," published by the Working Group on ApoE and Alzheimer Disease, formed jointly by the American College of Medical Genetics and the American Society of Human Genetics, in the *Journal of the American Medical Association* 274: 1627–29 (1995). Review articles which survey studies of amyloid proteins or genes include Checler 1995, and Hendriks and Van Broeckhoven 1996. Articles which discuss the potential relationship between ApoE isoforms and amyloid plaque formation, or which provide general overviews of genetic testing in Alzheimer's disease, include Pericak-Vance and Haines 1995, Gearing et al 1996, and Polvikoski et al 1996.

At present, familial forms of Alzheimer's disease are recognized in which a genetic mutation that gives rise to the disease manifestations is inherited within families. By performing genetic analysis on members of such families, it is possible to identify, prior to onset of clinical symptoms, those members who have the genetic mutation and are, therefore, destined to develop the disease. Other forms of Alzheimer's disease (often referred to as "sporadic Alzheimer's disease") that do not show the familial inheritance pattern cannot be diagnosed with certainty, in advance, by detecting a single genotypic trait. Rather, it is thought that multiple risk factors act in concert to cause the disease in sporadic cases. An unfavorable apolipoprotein E allele is one such risk factor which can currently be identified by genetic analysis to permit identifying individuals who are at increased risk of developing sporadic Alzheimer's disease. As more risk factors become known, it will become possible to predict with increased certainty those individuals who are destined to develop sporadic Alzheimer's disease.

In genetic studies, the focus of research attention is mainly on trying to figure out how various genes and proteins (and possibly other factors) lead to amyloid plaque formation in the brains of Alzheimer patients. In general, genetic researchers studying Alzheimer's disease have shown little or no apparent inclination to incorporate the thinking of the excitotoxicity school into their hypotheses regarding the pathogenesis of neuronal degeneration in Alzheimer's disease. Currently, efforts by genetic researchers to explain how genetic factors can cause all of the neuropathological manifestations of Alzheimer's disease are at an impasse. The fact that amyloid plaques do not distribute in the same brain regions as the neurofibrillary tangles and degenerating neurons is a major contradiction that these researchers have not managed to resolve.

Excitotoxicity school

Other neurologists, who can be termed "excitotoxicologists," have maintained that the neurotoxic properties of glutamate may play a critical role in the neuropathological manifestations of Alzheimer's disease. One of the Applicants herein (Prof. John Olney) can be considered one of the founders of this school; the term "excitotoxicity" was first coined by Olney in the early 1970s.

The main hypothesis that has been embraced by the excitotoxicity school of thought (including the Applicants, until recently) is that neuronal degeneration in Alzheimer's disease results from an excitotoxic mechanism involving excessive activation (i.e., hyperactivation) of NMDA receptors; this condition is referred to herein as NR/hyper. This school originally proposed that an NR/hyper mechanism might be operative throughout all stages of Alzheimer's disease; this was their attempt to explain the neuronal degeneration occurring in all stages. In the late 1980's and early 1990's, a number of excitotoxicologists, including the Applicants, published review articles propounding this hypothesis (see, e.g., Henneberry et al 1989; Olney 1989; Albin and Greenemayre 1992; and Beal 1992).

Today, researchers in the excitotoxicity school have not abandoned this position, but they have encountered a problem with it, which they have not figured out how to resolve. The problem is that recent evidence documents that in the aging brain, the NR system is not in a hyperactive condition; rather, with advancing age it becomes hypoactive (i.e., less than normally active). If, as they originally proposed, the NR system in Alzheimer's disease were in a hyper condition, it would be appropriate to treat this condition with an NMDA antagonist drug to suppress NR and thereby correct the hyper condition. However, if the NR system in Alzheimer's disease is already in a hypo condition, treatment with an NMDA antagonist drug would not seem to make any sense, because there is not any NR/hyper condition to correct. Therefore, the excitotoxicology school can also be described as being at an impasse; they currently are not able to recommend an effective treatment approach for patients with Alzheimer's disease.

Very recently, the Applicants have made new discoveries that provide a solution to the above problem. Their recent findings have caused them to realize that NR/hyper is only a relevant mechanism to explain a certain limited pathological process that occurs very early in Alzheimer's disease, prior to the onset of outwardly detectable symptoms. They now realize that in this early period, the disease process is undergoing a transformation, in which the NR/hyper mechanism effectively "burns out" and destroys a number of NMDA receptors; this type of burnout damage leaves those damaged neural circuits in an NR/hypo condition, in which they can no longer adequately respond to normal levels of stimulation by glutamate. As described elsewhere, the damaged NR/hypo condition then becomes a disease mechanism capable of destroying certain target neurons in various regions of the brain.

Thus, the initial NR/hyper state undergoes a transformation into its exact opposite—an NR/hypo state. This apparently paradoxical opposite condition then becomes responsible for the widespread neurodegeneration that occurs in Alzheimer's disease.

Based on this new realization, a rational therapeutic program consisting of two sequential treatment approaches has now been recognized by the Applicants.

First, in the presymptomatic stages of the disease, an NMDA antagonist drug (plus a safener drug to prevent the neurotoxic side effects of the NMDA antagonist, unless the NMDA antagonist drug is inherently safe due to one or more additional receptor activities) is appropriate to prevent the NR/hyper process from burning out NMDA receptors and producing the NR/hypo state.

However, this is an appropriate approach only if instituted before the hyper-to-hypo shift at NMDA receptors has substantially taken place. After the shift has substantially occurred (i.e., after the NMDA receptor system has been damaged to a point where it is in a permanently NR/hypo condition), treatment with an NMDA antagonist would be contraindicated, because it would pose a risk of driving the NR system even deeper into a more profoundly NR/hypo state, thereby accelerating the second-stage type of damage that is caused by the NR/hypo state.

By the time outward symptoms of Alzheimer's disease become evident, some degree of neuronal damage has already begun to occur inside the brain. Based on the Applicants' recent discoveries, the onset of outward displays of Alzheimer-type damage is regarded by the Applicants as a transition point. At this transition point, an NR/hypo condition is presumed to have arisen inside the brain, and has initiated a brain damage process which, if not arrested, will cause increasingly more widespread degeneration of neurons throughout many cortical and limbic regions of the brain.

Accordingly, beginning at this transition point and continuing for the remaining course of the disease (which will be the remainder of the patient's life, in most cases), the appropriate treatment should avoid any use of NMDA antagonist drugs. Proper treatment, beginning after outward displays of Alzheimer-type damage have commenced, will use one or more of the drugs referred to herein as "safener drugs", which can counteract and prevent the type of brain damage caused by the NR/hypo mechanism, as evidenced by the ability of such drugs to block the toxic side effects of NMDA antagonist drugs such as phencyclidine or MK-801.

A transition point which is determined as described above, relying on the appearance of outwardly visible signs of the disease, offers a useful approximation to indicate when it becomes proper to withhold NMDA antagonist drugs and administer only safener drugs to a patient. However, it should be recognized that this is only an approximation. Now that the NMDA receptor mechanisms, and the sequence of damage-causing steps involved in Alzheimer's disease, have been described herein, neurologists are likely to develop more precise methods of determining when a condition of substantial NMDA receptor hypofunction has arisen in the brain of a specific patient. Methods for improving the accuracy and sophistication of determining the transition point for Alzheimer patients include neuroimaging methods such as PET scanning, magnetic resonance imaging, and magnetic resonance spectroscopy, and sophisticated cognitive tests, as described in articles such as Morris 1993 and Morris et al 1988.

Accordingly, one object of the present invention is to disclose a new model for understanding the pathology of Alzheimer's disease. This is a model that other neurologists studying Alzheimer's disease do not currently share, because their prior research has led them in different directions, and because they are unaware of certain items of relevant information being disclosed herein for the first time.

Another object of this invention is to disclose an appropriate treatment for Alzheimer's disease during its presymptomatic stages. During this very early stage of the disease, an NMDA antagonist drug should be administered, to prevent burnout of the NMDA receptors in the glutamate-driven control system. Unless the NMDA antagonist has a built-in safener activity (because of activity at a second class of neuronal receptors), the NMDA antagonist drug should be accompanied by a "safener" drug, to prevent the toxic side effects that would be caused by the NMDA antagonist drug in the absence of any safening activity.

Another object of this invention is to disclose a completely different treatment for Alzheimer's disease, after a substantial level of NMDA receptor damage has occurred and an NR/hypo condition has arisen in the brain. Once a patient reaches this stage, any NMDA antagonist drug should be terminated. Proper treatment to prevent subsequent damage to pyramidal and other "target" neurons discussed herein will consist of a safener drug alone. Such safener drugs, which can prevent neuronal damage caused by drug-induced NMDA receptor hypofunction, can also prevent neuronal damage caused by endogenous NMDA receptor hypofunction which is occurring as a disease process in the brains of patients who are suffering from Alzheimer's disease.

These and other objects of this invention will be clarified and explained in the following summary and description.

SUMMARY OF THE INVENTION

Applicants have discovered a neuronal disease process involving a series of steps that apparently occur in Alzheimer's disease. This discovery offers a method of treating Alzheimer's disease, not just with palliatives, but in a manner that can actually prevent the progressive degeneration caused by Alzheimer's disease.

In a healthy brain, a neuronal system involving glutamate and NMDA-type glutamate receptors drives certain inhibitor neurons, causing them to release GABA and other inhibitory neurotransmitters. This controls and restrains certain downstream exciter neurons. During the very early, presymptomatic stages of Alzheimer's disease, NMDA receptors on the inhibitory neurons become "burned out" by excessive stimulation. During this presymptomatic stage, NMDA antagonist drugs should be administered, to protect the NMDA receptors against burnout damage.

Since NMDA antagonist drugs cause a condition known as NMDA receptor hypofunction (NR/hypo), which can cause toxic side effects that damage neurons in corticolimbic regions of the brain, these drugs should be co-administered with "safener" drugs to prevent the toxic side effects. Such safener drugs include various known drugs that can (1) suppress activity at kainic acid, m3 muscarinic, or sigma receptors, or (2) increase activity at type A GABA, 5HT-2A serotonin, or alpha-2 adrenergic norepinephrine receptors.

If NMDA receptors are not adequately protected against burnout damage during early Alzheimer's disease, damage to these receptors causes an endogenous NR/hypo condition, and these receptors can no longer respond to normal glutamate stimulation. This endogenous NR/hypo condition leads to "disinhibition", in which the glutamate-driven inhibitor neurons can no longer release enough GABA and other inhibitors to control and restrain the downstream excitor neurons.

When this stage is reached, administration of NMDA antagonist drugs should be stopped, since these drugs can worsen the NR/hypo condition, and would aggravate and accelerate the neuronal damage and degeneration caused by Alzheimer's disease. However, treatment with the safener drugs should continue, presumably for the remainder of the patient's life, to protect the corticolimbic regions of the brain against the endogenous NR/hypo condition that occurs in Alzheimer patients.

Therefore, this invention discloses a multi-faceted method for treating Alzheimer's disease. In the very early presymptomatic stages, treatment should use NMDA antagonist drugs along with "safener" drugs. During this stage, the patient should be carefully monitored, to determine whether NMDA receptor burnout and a condition of endogenous NR/hypo has arisen in the patient's brain. If such a condition has arisen, the NMDA antagonist drugs should be discontinued, to prevent worsening of the NR/hypo condition, while safener drugs should be continued, to protect the corticolimbic regions of the brain.

BRIEF DESCRIPTION OF THE DRAWINGS

FIG. 2 is a simplified depiction of transmitter-receptor pathways in the brain of an Alzheimer's patient who has suffered neuronal damage that has progressed to a point where the patient is displaying outwardly visible symptoms of the disease. The NMDA receptors on inhibitor neurons 20–50 have been "burned out" and are no longer functioning properly. Because of this damage, the inhibitor neurons no longer release their inhibitory transmitters in response to glutamate released by glutamate control neuron 10. When inhibitor neurons 20–50 can no longer control exciter neurons 60–80, the exciter neurons begin causing toxic overexcitation of target neuron 100. This can damage or kill the target neuron.

DESCRIPTION OF THE PREFERRED EMBODIMENTS

Figure 1:
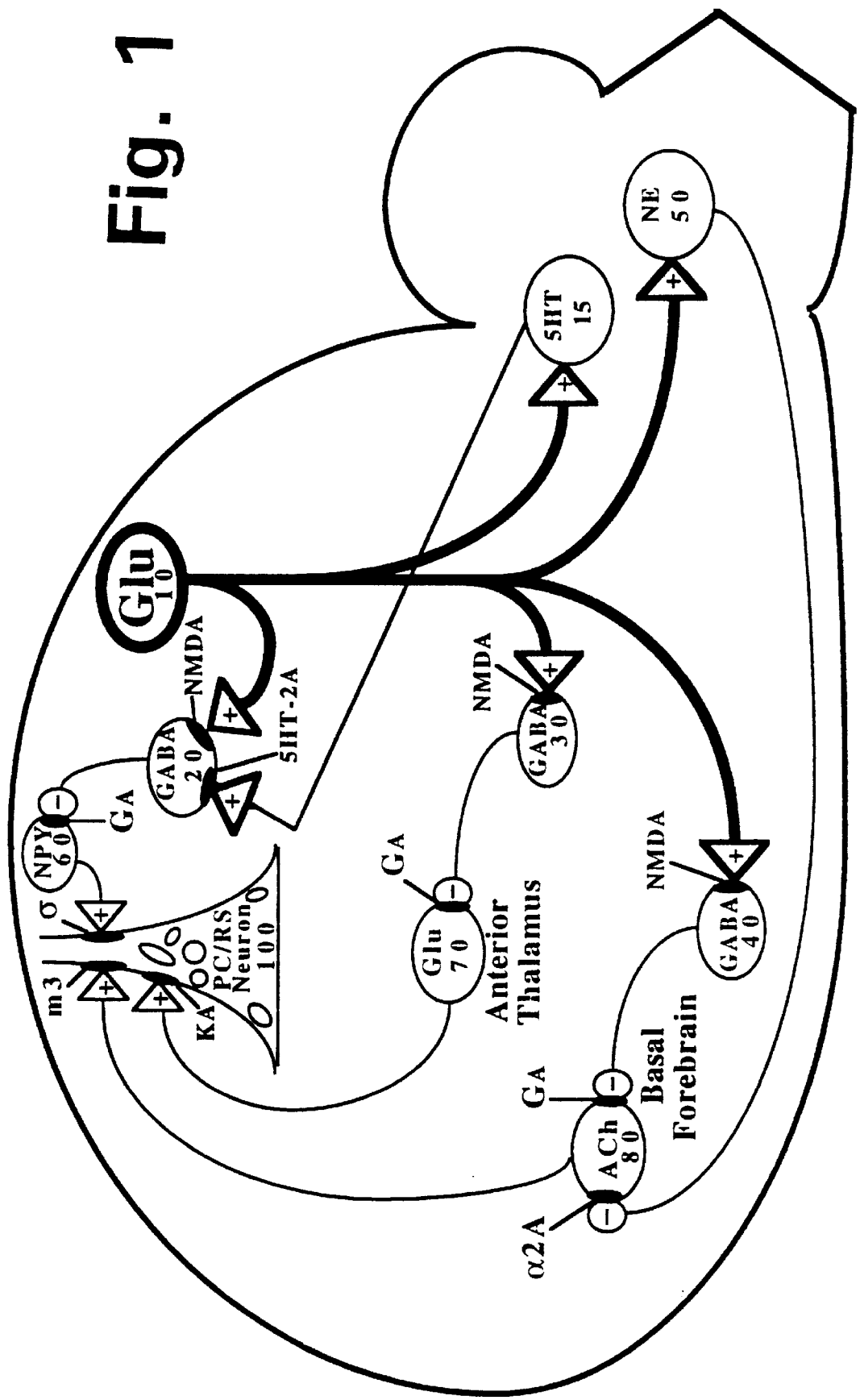
FIG. 1 is a simplified depiction of several transmitter-receptor pathways in a healthy brain. In this system, a glutamate control neuron 10 releases glutamate, which stimulates NMDA receptors on several inhibitor neurons 20–50. This causes the inhibitor neurons to release inhibitory neurotransmitters (mainly GABA, but also norepinephrine). The inhibitory neurotransmitters help suppress unwanted excitation of exciter neurons 60–80. This glutamate-driven inhibitory control of the exciter neurons helps protect a target neuron, shown as a pyramidal neuron 100 in the posterior cingulate or retrosplenial (PC/RS) cortex.

New drug treatments are disclosed herein for treating Alzheimer's disease. These treatments involve either of two drug regimens, depending on whether an Alzheimer's patient is in (1) the presymptomatic stages of the disease, or (2) the symptomatic stages of the disease.

In this context, terms such as "treatments" or "treating" are used broadly, to include preventing, retarding, or otherwise reducing the neuronal damage and/or the cognitive, memory, or behavioral disruptions that are caused or aggravated by Alzheimer's disease. "Chronic" administration refers to administration of a drug over a prolonged period, such as months or years, rather than merely until a specific situation has been healed or cured, as occurs after an injury or infection. In practical terms, unless and until a better mode of treatment for Alzheimer's disease is discovered, the preferred mode of chronic administration of the drugs described herein, to Alzheimer's patients, refers to administration of at least one neuroprotective drug to the patient, on a therapeutically continuous basis, for years, and presumably for the patient's entire remaining life, to stave off a threat of neuronal damage due to a dangerous neurotoxic condition that has arisen inside the patient's brain.

Early Stage Treatment

As used herein, the "early" or "presymptomatic" stage of Alzheimer's disease is deemed to exist so long as external symptoms and manifestations of the disease have not yet become apparent in someone who has been diagnosed as suffering from the disease (presumably through diagnostic methods such as genetic analysis or brain scans). As used herein, "external symptoms and manifestations" include memory loss, cognitive deficits, or behavioral disorders which rise to a level where a trained clinical practitioner attributes them to neuronal deterioration due to Alzheimer's disease.

During the presymptomatic stages of the disease, NMDA receptors on "inhibitory neurons" (discussed below and depicted in FIGS. 1 and 2) are being damaged, presumably due to overexcitation of the NMDA receptors by glutamate. During this stage, proper treatment to prevent damage to the NMDA receptors involves use of a combination of two drugs: (1) an NMDA antagonist drug, and (2) a safener drug. The NMDA antagonist drug provides a primary therapeutic benefit, by preventing NMDA receptors from being damaged by overstimulation. The safener drug provides a secondary therapeutic benefit, by preventing certain types of neurotoxic side effects that are caused by NMDA antagonist drugs in the absence of such safeners.

It should be recognized that there are several drugs that have both (a) NMDA antagonist activity, and (b) a built-in safener effect, due to activity at some other type of receptor. In the brains of healthy lab animals, these "inherently safened" NMDA antagonists do not cause the vacuoles and other toxic side effects that are caused by NMDA antagonists such as PCP and MK-801, because of activity at the additional neuronal receptors. Such drugs, and the receptors they interact with in addition to NMDA receptors, include the following:

(1) Ibogaine, which also suppresses excitatory activity at sigma receptors (Mach et al 1995; Popik et al 1995) and which may also be active at serotonin receptors (Mash et al 1995). Unlike nearly all the other NMDA antagonists discussed herein, which are synthetic drugs, ibogaine is obtained from a plant called *Tabernanthe iboga,* found in Gabon, in Africa. It has been known since the 1800's as having psychostimulant properties at low doses, and it can induce a hallucinatory state at high doses. It has long been used in the Gabonese society for initiation ceremonial rites, and it is being studied actively by Western medicine because of claims that it can help reduce cravings among people addicted to drugs such as cocaine, heroin, nicotine, and alcohol (see U.S. Pat. Nos. 4,499,096, 4,587,243, 4,857,523, 5,152,994, and 5,026,697, issued to Lotsof). It has two closely related analogs, ibogamine and tabernanthin, which have also been isolated from the same family of African plants, and which are believed to have similar neuronal activities inside the brain. All three compounds are listed in the Merck Index.

(2) Eliprodil, which also increases inhibitory activity at sigma receptors (Contreras et al 1990, and Carter et al 1988 and 1989).

(3) Certain anti-cholinergic drugs such as procyclidine, trihexyphenydyl, and biperiden, which also suppress excitatory activity at muscarinic acetylcholine receptors (Olney et al 1987).

(4) Certain quinoxalinediones, including NBQX, ACEA 1021, and ACEA 1031, which are discussed below, and which suppress activity at non-NMDA receptors (i.e., kainic acid receptors and AMPA receptors), in addition to NMDA receptors. As described in Example 11, NBQX blocks non-NMDA receptors so strongly that it acts as a safener agent when co-administered with MK-801. Accordingly, these and other quinoxalinediones are of great interest to pharmaceutical companies, and offer strong promise as inherently safened NMDA antagonists.

However, despite the availability of such drugs, the safest and most prudent course of action (until future research indicates otherwise or results in totally safe NMDA antagonists) for treating Alzheimer patients should include at least some quantity of a known safener drug. This is because an Alzheimer patient is, presumably, already suffering from some sort of disease process or elevated risk factor which is placing the relevant NMDA receptors, on the inhibitor neurons shown in FIGS. 1 and 2, at a substantially elevated risk of sustaining burnout damage, leading to an NR/hypo condition. Safener drugs therefore are prudent and appropriate for treatment of presymptomatic Alzheimer patients, even when low-toxicity NMDA antagonists are used, to minimize this elevated risk factor and provide a better margin of safety.

It should be noted that low-toxicity NMDA antagonists offer good candidates both for treating Alzheimer's disease, and for additional developmental research to identify analogs having adjusted balances in their dual or multiple receptor binding affinities. For example, the antiparkinsonian agents procyclidine, trihexyphenydyl, and biperiden all have affinities for muscarinic receptors that are several times higher than for NMDA receptors. With proper screening by means of receptor binding assays in in vitro tests, analogs having alternate substituents at certain locations in any of these molecules can be developed which have either roughly equal affinities for NMDA receptors and muscarinic receptors, or which have higher affinity for NMDA receptors than for muscarinic receptors. Such analogs would provide neurologists with an improved array of options for treating Alzheimer patients, and neurologists would be able to select an agent which has the best combination of receptor binding affinities for any specific patient.

Treatment After External Symptoms Become Apparent

By the time significant and outwardly visible symptoms of Alzheimer's disease begin to be displayed by a patient (this is referred to herein as the "symptomatic" stage of Alzheimer's disease; it lasts from the time such outward symptoms to appear, until the death of the patient), it is clear that the patient has already suffered a substantial level of internal neuronal damage in his or her brain.

Based on the neuronal mechanisms set forth herein, and unless sophisticated brain scanning technology indicates otherwise in a specific patient, it is presumed that such damage includes (although it may not be limited to) substantial damage to substantial numbers of NMDA receptors. When this stage has been reached, then the condition referred to herein as NR/hypo has been reached, and a different form of damage begins to occur. This type of damage involves the death of "target neurons" (described below) in certain corticolimbic regions of the brain. The mechanism by which this occurs is discussed below and depicted in FIGS. 1 and 2.

Once a symptomatic stage of Alzheimer's disease has arrived, where substantial damage has been done to NMDA receptors and a condition of NR/hypo exists inside the brain, NMDA antagonist drugs are no longer advisable and useful to protect the already-damaged NMDA receptors. Indeed, such drugs might aggravate the severity of the NR/hypo condition, and thereby accelerate subsequent damage to other neurons.

Accordingly, the drug treatment that becomes appropriate, after NMDA receptors have already been damaged in the brain of an Alzheimer victim, uses one or more of the same safener drugs which can protect against the neurotoxic side effects of NMDA antagonist drugs in lab animals. In lab animals that have been administered NMDA antagonist drugs, and in humans suffering from Alzheimer's disease, these safener drugs protect a class of vulnerable pyramidal and other corticolimbic neurons, referred to herein as "target neurons", as discussed below.

Relevant Receptor-Transmitter Pathways

In the neural circuitry that is relevant to the present invention (depicted in a simplified schematic manner in FIG. 1 and FIG. 2), there is an array of different neurons which can be regarded as falling into four sequential stages. The following terms have been created to describe these four different stages: (1) glutamate control neurons; (2) inhibitor neurons; (3) exciter neurons; and (4) target neurons. The neurons in each stage release neurotransmitters which contact, and either stimulate or inhibit, the neurons in the subsequent stage.

At the start of this circuit is a "glutamate control neuron" 10, which releases glutamate in tiny amounts, but on a continuous or nearly continuous basis. The glutamate is released at an array of synapses that emerge from glutamate control neuron 10.

This glutamate neuron contacts and activates NMDA receptors on the surfaces of second stage neurons called "inhibitor neurons" 20, 30, and 40 (as well as neurons 50 and 90, discussed below). The three inhibitor neurons 20–40 are called "GABAergic" neurons, since they release GABA (gamma amino butyric acid, an inhibitory neurotransmitter) when the GABAergic neurons are activated. Other inhibitory neurons, which release other transmitters such as serotonin or norepinephrine, are discussed below.

The slow, steady release of GLU by glutamate control neuron 10 provides a steady, continuous driving force that keeps inhibitor neurons 20–40 in a constant state of activity, resulting in continuous or nearly continuous release of GABA.

The GABA which has been released by the inhibitor neurons 20–40 contacts GABA receptors on the surfaces of "exciter neurons" 60, 70, and 80, each of which releases a different type of excitatory transmitter. Exciter neuron 60 releases neuropeptide Y (NPY); exciter neuron 70 releases glutamate; and exciter neuron 80 releases acetylcholine (ACh).

All three of the exciter neurons 60, 70, and 80 are coupled, via axons, to a pyramidal neuron 100, located in the posterior cingulate or retrosplenial (PC/RS) cortex of the brain. If all three of the excitatory neurons 60, 70, and 80 begin firing simultaneously, they can overstimulate pyramidal neuron 100 and push it to the point where it becomes so exhausted that it begins to suffer serious damage and eventually dies from overstimulation. Accordingly, pyramidal neuron 100 is labelled herein as a "target neuron", since it can be destroyed if hit by too many "bullets" released by the exciter neurons. As discussed below, pyramidal neurons in the PC/RS cortex are merely one type of target neurons; they are highly vulnerable and consistently damaged when NMDA antagonists are administered to lab animals, so they are usually studied and analyzed as a highly sensitive indicator of excitotoxic damage. Other types of neurons in other regions of the brain also suffer similar damage (albeit, usually to a lesser degree), and are also target neurons.

The pyramidal target neuron 100 is shown as having three different types of excitatory receptors: (1) kainic acid receptors, a type of non-NMDA glutamate receptor; (2) m3 receptors, a type of acetylcholine muscarinic receptor; and, (3) sigma receptors, which are believed to be triggered by neuropeptide Y (NPY). The presence of all three types of excitatory receptors on pyramidal neurons is supported by experimental evidence gathered by the Applicants, who have shown that if activity at any one of these three classes of receptors is blocked, then any damage to pyramidal neurons, by NMDA antagonist drugs, is greatly reduced or entirely prevented.

Thus, glutamate stimulates various GABAergic neurons to release GABA, an inhibitory transmitter. This glutamate-driven slow, steady release of GABA establishes a condition which neurologists call "tonic inhibition", which helps restrain and limit the activity of several downstream excitatory paths. The phrase "tonic inhibition" implies that this mechanism maintains an inhibitory tone in the system.

This type of tonic inhibition represents an important principle (and an apparent paradox) of CNS activity. An excitatory neurotransmitter, such as glutamate, can cause suppression, rather than excitation, of neuronal activity. This is important for sustaining various cellular functions in the CNS, and malfunctions in this system lead to a problem called "disinhibition", which can contribute to dysfunction and degeneration of neurons in the brain of an animal or human suffering from NMDA receptor hypofunction (NR/hypo).

Specifically, if the NMDA receptors which govern GABAergic neurons 20, 30, and 40 (and norepinephrine neuron 50), as shown in FIGS. 1 and 2, are blocked by an NMDA antagonist drug, or if they are rendered hypofunctional by a disease process which has left the NMDA receptors on neurons 20–40 "burned out", then the ability of glutamate control neuron 10 to tonically inhibit the downstream "exciter" neurons 60, 70, and 80 (via GABAergic neurons 20, 30, and 40) is lost. This loss of glutamate-mediated control is referred to herein as "disinhibition", since it interferes with the inhibitory mechanism that normally protects pyramidal neuron 100. When disinhibition occurs due to NMDA receptor hypofunction, all three excitatory neurons 60, 70, and 80 can begin to overstimulate pyramidal neuron 100, and may push it to a point where it becomes so exhausted that it suffers serious damage and eventually dies from overstimulation.

In summary, if NMDA receptor hypofunction (NR/hypo) affects inhibitory neurons 20–40, it can endanger and lead to the death of various target neurons, such as pyramidal neuron 100.

The schematic diagram in FIG. 1 also depicts an inhibitory neuron 50 located in the brain stem. When stimulated by glutamate, neuron 50 will normally secrete norepinephrine (NE) into the forebrain, via long fibrous processes. This is an additional regulatory mechanism for controlling the release of acetylcholine (ACh) from neuron 80. If the NMDA receptor on NE neuron 50 is blocked or suppressed, so that glutamate cannot drive the inhibitory neuron 50 and cause it to release NE, its inhibitory action is turned off (disinhibited). This releases the ACh neuron 80 from its inhibitory control mechanism.

The schematic diagram in FIG. 1 also includes a neuron 15, located in the midbrain, which can release 5-hydroxytryptophan (5HT, also called serotonin). Normally, when stimulated by glutamate, neuron 15 secretes serotonin through a long fibrous process onto a 5HT-2A receptor on GABA neuron 20. This is an additional mechanism by which glutamate normally effects tonic inhibition, which sets the stage for yet another form of disinhibition if the inhibitory mechanism fails.

The highly simplified depiction in FIG. 1 indicates that a single glutamate-releasing neuron 10 interacts with all four inhibitory neurons 20, 30, 40, and 50. This depiction is used merely to avoid clutter in the drawing. In the brain of any mammal, thousands or millions of glutamate-releasing neurons will interact to sustain tonic inhibition of neuronal circuits involving thousands or millions of inhibitory neurons.

Similarly, the single target neuron 100 shown in FIG. 1 merely represents one of thousands or millions of neurons which are placed at risk when NMDA receptors no longer function at normal and proper levels, and the endangered neurons are scattered widely throughout a number of corticolimbic regions of the brain. The PC/RS cortical region has been the focal point of the examinations described in the Examples, because it is one of the most heavily damaged portions of the brain, and one of the most consistent and reliable areas for measuring and quantifying damage. This is not meant to imply that it is the only area damaged or at risk. On the contrary, many other neurons in many other brain regions are also at risk.

Evidence To Support The Applicants' Interpretations

Several types of experimental evidence have been gathered by the Applicants to support their conclusions involving NR/hypo as a causative mechanism in Alzheimer's disease. These new findings, and the conclusions that they point to, also help explain a number of other observations that had been made and published previously, both by the Applicants and by other researchers. Accordingly, when these realization moved into position, they provided a framework for analyzing and correlating a number of observations and reports that previously had been scattered and disparate, and in some cases contradictory to the general trends of thought on Alzheimer's disease.

The relevant observations indicate that NR/hypo apparently can reproduce many of the same neuropathological patterns shown in Alzheimer's patients. Several hallmark characteristics of Alzheimer's disease, which distinguish it from other neurodegenerative diseases, can be described as follows:

1) Relatively early in the disease process, beta amyloid protein is deposited in various brain regions. This leads to the formation of what are called "amyloid plaques".

2) Neurons in many other brain regions (i.e., regions that are different from where amyloid plaques are deposited) develop corkscrew-like deformities of their dendritic processes; these deformities are called "neurofibrillary tangles".

3) The neurons that develop neurofibrillary tangles progressively degenerate, unto death, so that there is a marked loss of neurons in the same distribution pattern as the distribution of neurofibrillary tangles.

4) Synaptic complexes (specialized membrane sites where one neuron contacts another for information transfer) are markedly decreased, so that loss of synaptic complexes is considered a hallmark of Alzheimer's disease.

5) As neurons degenerate, they synthesize a protein that is not normally synthesized by healthy neurons. This protein is called "heat shock protein-72 Kda", where 72 Kda refers to its molecular weight of 72 kilodaltons.

The Applicants' recent findings demonstrate that the NR/hypo neurodegenerative process, which can be induced in mammalian brains by administering NMDA antagonist drugs, precisely reproduces or closely mimics nearly every fundamental feature of the neuropathology of Alzheimer's disease.

The specific features of Alzheimer's disease, in humans, that are closely reproduced on a cellular and structural level inside the brain when NMDA antagonist drugs are administered to lab animals, include the following:

A) Loss of synaptic complexes

The Applicants have discovered that early in the NR/hypo neurodegenerative syndrome, after NMDA antagonist drugs are administered to a lab animal, dendritic spines (the nerve cell components where most of the synaptic complexes are located) swell massively and selectively degenerate, so that many of the synaptic complexes on these dendritic surfaces are destroyed. This reproduces, and provides an excellent explanation and model for, the loss of synaptic complexes in patients suffering from Alzheimer's disease.

B) Loss of neurons

The Applicants have discovered that in a later stage of NR/hypo neurodegeneration caused by administration of NMDA antagonist drugs, many of the neurons that suffered from swelling of their dendritic spines, in the early stages, will undergo a slow degenerative process, which for many neurons ends in cell death. This reproduces, and provides an excellent explanation and model for, the death and loss of neurons in patients suffering from Alzheimer's disease.

C) The patterns of neuronal degeneration in Alzheimer's disease are reproduced by administration of NMDA antagonist drugs The neurons that degenerate, in the brains of people who suffer from Alzheimer's disease, are specific neurons which have two characteristics: (1) they have a pyramidal or multipolar shape, and (2) they are distributed in certain layers of the cerebral cortex, or in certain clusters within various limbic brain regions.

The Applicants have discovered that the neurons which degenerate, after NMDA antagonist drugs are administered to induce NMDA receptor hypofunction, are pyramidal or multipolar neurons, distributed in the same layers and in the same regions of the cerebral cortex that are damaged in Alzheimer's disease, and in the same clusters within the limbic brain regions that are damaged in Alzheimer's disease. Thus, both the specific neuron types, and the specific brain regions affected in Alzheimer's disease, are the same as those destroyed by the NR/hypo mechanism which can be induced in lab animals by administering NMDA antagonist drugs.

D) Neurofibrillary tangles

The corkscrew-like deformities that are observed, throughout corticolimbic brain regions, in neurons that have degenerated due to Alzheimer's disease, are also found throughout corticolimbic brain regions in neurons that are destroyed by the NR/hypo mechanism in animals that have received NMDA antagonist drugs.

E) Heat Shock Protein 72-Kda

The same 72 kilodalton heat shock protein that is abnormally expressed by neurons that degenerate in Alzheimer's disease, is also abnormally expressed by neurons that are induced to degenerate by the NR/hypo mechanism when induced by NMDA antagonist drugs. Using monoclonal antibodies that bind specifically to the 72-Kda heat shock protein in an immunocytochemical labeling procedure, the Applicants have shown that the same pattern of heat shock protein expression that occurs in Alzheimer's disease, also occurs in drug-induced NR/hypo.

F) Amyloid plaques

Amyloid plaque formation is the single major feature of Alzheimer's disease that is not reproduced, in a closely-mimicked fashion, by drug-induced NR/hypo. However, in light of additional relevant information, this serves as evidence to corroborate the Applicants' assertions herein, since the amyloid pathology that occurs in the brains of Alzheimer's patients results from a genetic predisposition that is present in those patients, but not in laboratory rats.

It has been shown in in vitro experiments that when beta amyloid is introduced into the environment of cultured neurons, it causes glutamate receptors on the cultured neurons to become hypersensitive to the excitotoxic action of NMDA, and results in the destruction of these neurons and their NMDA receptors. According to the Applicants' interpretation, this same mechanism that has been observed in test tube experiments is operative in the in vivo brains of patient; suffering from Alzheimer's disease. These patients have a genetic predisposition that causes beta amyloid very early in the disease to accumulate in their brain where it interacts with NMDA receptors, causing those receptors to become hypersensitive to excitotoxic stimulation and prone to sustain injury even when stimulated by physiological concentrations of glutamate. This excitotoxic injury can damage or destroy the membrane sites where the NMDA receptors are located, and in severe cases it can destroy entire receptor-bearing neurons (including all NMDA receptors on the dead neurons). In either case, NMDA receptors are damaged or destroyed, and the NMDA receptor system is thereby rendered hypofunctional.

It is known to other neurologists studying Alzheimer's disease that beta amyloid protein can cause NMDA receptor hyperactivity. However, it appears that no other neurological researchers studying Alzheimer's disease have drawn the same conclusions that the Applicants have set forth herein.

Lack of Acceptance of the NR/hypo Concept Among Other Alzheimer Researchers

It is worth emphasizing that the Applicants' assertions herein have not previously been proposed or given serious attention by other researchers in the Alzheimer's field. There are a number of apparent reasons why other Alzheimer researchers have not come to the same realizations as the Applicants, and have not proposed that the NR/hypo mechanisms described herein play a key role in Alzheimer's disease. These reasons include the following:

1. When the ability of NMDA antagonists to damage animal brains was first described by the Applicants (Olney et al., 1989), it was believed that the damage was limited to a reversible vacuole reaction affecting only a small cluster of neurons in the PC/RS cortex. It was reported several years later, by a research team that included one of the Applicants (Fix et al 1993) that a high dose of an NMDA antagonist could cause PC/RS neurons to degenerate unto death; however, it was still assumed that the damage was limited to a relatively few PC/RS neurons. Neither the Applicants nor anyone else assumed that a brain damage syndrome limited to this small group of neurons could have any relevance to the much more widespread pattern of brain damage in Alzheimer's disease.

In 1994, the Applicants described, in an abstract (Corso et al 1994), the ability of phencyclidine (an NMDA antagonist) to cause damage in regions other than the PC/RS cortex. However, the authors of that abstract pointed out that the damage which occurred outside the PC/RS region was only encountered in a very small percentage of treated animals. Again, no indication was given (or observed, in the laboratories) that the pattern of damage corresponded to the pattern of damage in Alzheimer's disease, or that neuronal damage caused by NMDA antagonists in animals could be considered an appropriate model for studying Alzheimer's disease.

Late in 1995 the Applicants reported, again in an abstract (Corso et al 1995), that a more consistent disseminated pattern of brain damage could be induced by PCP, if a small dose of pilocarpine was included in the treatment. However, in that 1995 abstract, it was stated that the full pattern and type of damage was under investigation. No suggestion was made that the degenerative syndrome might be relevant to Alzheimer's disease.

Thus, none of these publications from the Applicants' laboratory, documented (either individually or collectively) that the NR/hypo mechanism can induce the same type and pattern of neurodegeneration seen in Alzheimer's disease. The critical evidence that the NR/hypo mechanism induces a neurodegenerative syndrome that faithfully mimics the neuropathology of Alzheimer's disease is disclosed for the first time in this patent application, and has not been publicly communicated or published elsewhere.

The fact that this information has not yet been made public is a major reason why no neurologists studying Alzheimer's disease (other than the Applicants, who are privy to the unpublished data) currently embrace the view that an NR/hypo mechanism can explain the neuropathology of Alzheimer's disease.

2. It is well known that when humans are exposed to PCP, ketamine, or various other NMDA antagonists, they display a psychotic reaction, including symptoms such as hallucinations and delusions. It is also well known that the presenting symptoms of Alzheimer's disease are not psychotic symptoms, but rather are what neurologists refer to as dementing symptoms.

As suggested by the word, "de-menting" symptoms indicate that the mental faculties are being taken away, and lost. Such symptoms include memory loss, and loss of perceptual, analytical, or other cognitive abilities.

By contrast, "psychosis" indicates a derailment or diversion, rather than a loss, of a person's mental awareness and cognitive abilities. The classic examples of psychotic symptoms are hallucinations and delusions, rather than demented symptoms such a profound memory loss.

The profound difference between psychotic symptoms, and dementing symptoms, can be clearly and easily demonstrated by asking a patient with Alzheimer's disease, and a patient with schizophrenia, the following types of simple questions: What is the day, the month, and the year? What is your name, your doctor's name, and your sister's name? And what did you eat for breakfast? A schizophrenic (psychotic) patient, even in the advanced stages, can usually answer these questions accurately and without hesitation. By contrast, a patient suffering from Alzheimer's dementia can only respond with a vacant stare.

These distinctions are clear to any skilled neurologist, although they are sometimes confused by laymen, and even by some psychologists (e.g., Ellison 1994).

The NR/hypo state, when induced by NMDA antagonist drugs, is associated with psychotic symptoms, exemplified by the psychotic behavior of illegal drug users who are stoned on "angel dust" (which is phencyclidine, or PCP, a potent NMDA antagonist). The profound differences between PCP-type psychosis, and the losses of memory and cognition which characterize Alzheimer's disease, is a major reason why it apparently has not occurred to neurologists studying Alzheimer's disease that an NR/hypo mechanism, which is clearly known to be associated with drug-induced psychosis, might also be responsible for very different symptoms of a very different disorder. If an NR/hypo condition were an operative mechanism in Alzheimer's disease, then according to conventional thinking and presumptions, the presenting symptoms of Alzheimer's disease should typically involve psychotic symptoms, instead of dementing symptoms.

It should be noted that the Applicants do not consider the psychotogenic properties of NMDA antagonists an incongruity in their hypothesis. Rather, they believe that the NR/hypo mechanism may play a role in either psychotic or dementing disorders, depending on the components of the NR/hypo circuitry that are pathologically altered. According to the Applicants' analysis, a defect in certain components of the circuitry, especially if it occurs early in life (e.g., prenatally), would be conducive to onset of a schizophrenic psychosis in late adolescence or early adulthood (the full reasoning behind this assertion relating to schizophrenia is detailed in Olney and Farber 1995). By contrast, if the NR/hypo defect consists primarily of a disruption in other parts of the circuit, and if this NR/hypo defect is instilled relatively late in life (as suggested by the Applicants herein) as a disease mechanism that follows burnout damage to NMDA receptors, it will be conducive to onset in late adulthood of Alzheimer's dementia without psychotic manifestations.

3. The PC/RS cortex is the most sensitive area of the brain to damage by NR/hypo induced by administering NMDA antagonist drugs to lab animals. However, most researchers studying Alzheimer's disease have not considered this brain region to be prominently or even significantly involved in Alzheimer's disease. In a comprehensive review of the relevant literature, the Applicants discovered that, except for two publications noted below, no researchers have reported any significant involvement, or any significant lack of involvement, of the PC/RS cortex in the brains of people suffering from Alzheimer's disease (analyzed either by autopsy after death, or by various MRI, PET, or other scanning methods while still alive). The vast majority of studies on Alzheimer's disease have simply not looked at the PC/RS brain region. The neurologists who conducted those studies saw no reason to study that specific part of the brain.

There are two exceptions to this area of neglected research. First, a major study that was published 15 years ago (Brun and Englund 1981), and was apparently disregarded by subsequent researchers, identified the posterior cingulate cortex as a region which was heavily involved in Alzheimer's disease, and the anterior cingulate cortex as a region spared. This is the same distribution as the pathology that arises after NR/hypo damage induced by NMDA antagonist drugs; the posterior cingulate is preferentially damaged, while the anterior cingulate is preferentially spared. And second, a more recent study (Minoshima et al 1994) performed by PET scanning on living Alzheimer patients, early in the disease, showed that the posterior cingulate cortex is very heavily involved, early in the disease.

To the best of the Applicants' knowledge and belief, neither of these reports has received any special notice or recognition by Alzheimer researchers. There are many published reports pertaining to histological studies or brain scans in Alzheimer patients, and the focus of attention has almost invariably been on various other corticolimbic brain regions.

4. A major feature of the Applicants' NR/hypo concept is that it involves hyperactivity of the cholinergic muscarinic transmitter system. In fact, it holds that hyperactivity of m3 muscarinic receptors plays an important role in neurofibrillary tangle formation and neuronal degeneration in Alzheimer's disease. This is in direct contradiction to a widely held presumption in the Alzheimer research field, which holds that the cholinergic muscarinic transmitter system is not hyperactive, but rather is hypoactive in Alzheimer's disease.

It is widely believed that abnormally low (hypo) activity of the muscarinic cholinergic transmitter system plays a major role in the memory and other cognitive impairments in Alzheimer's disease. This belief is so strong that drug companies that are trying to develop drugs to treat Alzheimer's disease have been focusing almost exclusively on designing drugs that will increase the activity of the cholinergic transmitter system.

This line of research follows the partial success of tacrine, the only drug that is currently approved for the treatment of Alzheimer's disease. Tacrine inhibits the breakdown of acetylcholine, thereby increasing the duration of action of acetylcholine at cholinergic receptors. It is generally assumed in Alzheimer research that tacrine is beneficial for patients, because it leads to increased activation of muscarinic receptors in the cerebral cortex and hippocampus. Clearly, the desire (among pharmaceutical companies) to find ways to increase muscarinic activity is driven by a prevailing belief that the muscarinic system is Alzheimer patients has been suppressed, and does not have sufficiently high levels of activity.

The Applicants herein are suggesting the exact opposite, and in the Examples, below, extensive evidence is presented in support of the Applicants' position. The Applicants hope and believe this new evidence will either be fully borne out and will prove their assertions to be correct, or will at least provoke a very careful and painstaking reappraisal of the current presumptions and dogma about muscarinic activity in Alzheimer patients. What is clear, at the present time, is that the Applicants' assertion regarding abnormally high levels of muscarinic activity in Alzheimer patients directly contradicts the conventional beliefs and prior art, and points in the opposite direction.

Drugs for Preventing NR/hypo-Mediated Neuronal Damage in Alzheimer's Patients

This invention includes, and to a large extent rests upon, two discoveries: (1) the discovery by the Applicants that NR/hypo is a causal mechanism in Alzheimer's disease; and, (2) the realization that certain drugs which can block the toxic side effects of NMDA antagonists can also block or reduce the progressive brain damage that occurs in Alzheimer's disease.

To the best of the Applicants' knowledge, this is the first time that any of the drugs listed below have been seriously proposed as agents to reduce or slow the neuronal damage caused by Alzheimer's disease, by administering them over a prolonged period of time to a person who is suffering from Alzheimer's disease. Therefore, even though all of the drugs listed below are known drugs, and even though many of them were previously identified and disclosed as being able to block the toxic side effects of NMDA antagonists, the discovery that these drugs can effectively treat Alzheimer's disease is believed to be completely new.

It should be recognized that (1) the potency and efficacy of the drugs listed herein for treating Alzheimer's disease will vary, and (2) they will each cause certain types of side effects, which may be mild and tolerable in some patients but not in others. Accordingly, it should be understood that a physician who is treating a specific Alzheimer patient will need to determine the optimal drug treatment (or drug combination) for that patient, during any particular stage of the disease.

The fact that a number of different drugs, which act through different neuronal receptor pathways, offer good candidates for such treatment does not mean that this treatment is indefinite and undefined. Instead, it means that physicians and patients have an array of options, among drugs that were never previously recognized as being effective in reducing the progressive neuronal deterioration of Alzheimer's disease.

As mentioned previously, in the Background section, a number of different types of drugs have previously been disclosed as "safener" drugs, which can be used to accompany NMDA antagonist drugs, to reduce the toxic side effects of the NMDA antagonists. However, a number of those drugs (such as most barbiturates) are suitable only for crisis-type care, and would have unacceptable side effects if used on a long-term basis. In order to be useful for long-term administration, an Alzheimer's treatment drug cannot be heavily sedating or addictive, or have other unacceptable side effects.

The categories of "NMDA safener drugs" which are believed to offer good candidates for use to prevent the ongoing damage of Alzheimer's disease, and which are likely to have tolerable side effects for at least some patients when administered in suitable dosages under the care of a physician, include the following:

(1) Anti-cholinergic drugs which block the muscarinic class of cholinergic receptors, and in particular the m3 class of muscarinic receptors. Examples include atropine, benztropine, trihexyphenidyl, biperiden, procyclidine, benactyzine, and diphenhydramine. Scopolamine is also in this category. Although it should be regarded cautiously, since it is a powerful anticholinergic agent, it is widely used via delivery systems such as external skin patches. Accordingly, it may be suitable for some patients.

In addition, after it has been publicly disclosed that anti-cholinergic drugs which block m3 receptors can be used as Alzheimer's treatment drugs, there is likely to be an effort to develop anti-cholinergic drugs which specifically and selectively block activity at m3 receptors, without having substantial activity at any other cholinergic receptors. Since such drugs presumably would impose less disruption on the cholinergic system, they offer good promise as Alzheimer treatment drugs which may have fewer and milder side effects than anti-cholinergic drugs which block more cholinergic receptors than just m3 receptors.

The ability of anti-cholinergic drugs to act as safener agents when co-administered with NMDA antagonist drugs is described in more detail in Olney et al 1991, and in U.S. Pat. No. 5,034,400. (Olney 1991).

(2) Agents which increase activity at gamma-aminobutyric acid (GABA) receptors. Benzodiazepine drugs, which can increase ("potentiate") the effects of naturally-occurring GABA, have long been known to have some efficacy in preventing the toxic side effects of NMDA antagonists. For example, diazepam, which is sold under the trademark VALIUM, has been used for years to reduce the psychotomimetic "emergence reaction" that sometimes occurs in patients who are waking up from ketamine anesthesia after surgery.

In published items which relate to the use of NMDA antagonists in acute crisis situations such as stroke or cardiac arrest (e.g., U.S. Pat. No. 5,474,990, Olney 1995), it was asserted that benzodiazepine-type drugs were not adequate for such use in crisis situations such as strokes, since they can only potentiate the effects of GABA. If an adequate quantity of GABA is not present in an acute crisis, benzodiazepine-type drugs will not provide as much protection as can be provided by other known agents, such as secobarbital, pentobarbital, and certain other barbiturates, that can directly open chloride ion channels in GABAergic neurons even in the absence of naturally occurring GABA.

This is still believed to be true for acute crisis situations. However, powerful barbiturates such as secobarbital and pentobarbital would not be well-suited for long-term oral administration, unless analogs are developed and used which do not cause a heavy sedating effect.

Phenobarbital offers one example showing that such manipulation of barbiturates is entirely feasible. It is a relatively mild barbiturate, which has a long history of being chronically administered to patients for years, as an anti-convulsant and tranquilizer. It has some level of activity as a safening agent in preventing vacuoles when MK-801 is administered. Accordingly, analogs of various barbiturates might be developed which act as non-sedating barbiturates which can block the neurodegeneration caused by Alzheimer's disease. Phenobarbital offers an example of how the sedating property of some barbiturates can be greatly reduced without losing their other properties, enabling their use for chronic treatment.

Regardless of whether such analogs of barbiturates are developed, benzodiazepines (including diazepam and its various analogs) are believed to be well-suited in their current form for long-term use to reduce or retard the slow progressive neurodegeneration of Alzheimer's disease.

(3) In addition to benzodiazepines and barbiturates, certain other classes of agents are known that also increase activity at GABA receptors. These include certain agents currently used as anesthetics, such as isoflurane, halothane, and propofol (see, e.g., Ishimaru et al 1995 and Jevtovic-Todorovic et al 1995), and certain agents known as steroid anesthetics or neurosteroids, such as alfaxolone and ganaxolone.

The Applicants have tested isoflurane, halothane, and propofol against MK-801, and have shown that these drugs effectively block vacuole formation. They have not yet tested any steroid anesthetics or neurosteroids, but due to the activity of such drugs at GABA sites, the Applicants expect and assume that such agents will have substantial protective effects against vacuole formation. Accordingly, these classes of drugs offer interesting candidates for further exploration and development, to determine whether they (or their analogs) can have tolerably low anesthetizing effects while retaining mild but significant activity at GABA receptors. Such analogs of these anesthetizing compounds might be suitable for chronic use to reduce or retard the progression of Alzheimer's disease.

(4) A number of drugs are known to suppress activity at sigma receptors; accordingly, they can help protect target neurons against over-excitation involving neuropeptide Y. Such drugs include di(2-tolyl)guanidine and rimcazole, which are relatively selective for sigma receptors, as well as various other drugs, some of which are anti-psychotic agents, such as haloperidol, thioridazine and loxapine, which interact with dopamine receptors as well as sigma receptors.

(5) Drugs that act as agonists at a class of receptors called alpha-2 adrenergic receptors were also recently discovered, by the Applicants herein, to bloc), the toxic side effects of NMDA antagonist drugs. Drugs in this class include clonidine, p-iodoclonidine, guanabenz, guanfacine, xylazine, and lofexidine (Farber et al 1995a and 1995b). These drugs are believed to offer good candidates for treating Alzheimer's disease.

(6) Certain other drugs known as "atypical antipsychotic agents", including clozapine, olanzapine, and fluperlapine (Farber et al 1995c), act at various receptors, including dopamine, serotonin, and norepinephrine receptors. These drugs also bind to and act as antagonists at muscarinic receptors; accordingly, these drugs could be grouped either in an anti-psychotic category, or in the anti-cholinergic (muscarinic antagonist) category discussed above. Because of their combined activity at muscarinic receptors as well as certain other receptors, these drugs might be fairly potent in reducing the progressive damage caused by Alzheimer's disease. These drugs (and their analogs) can be evaluated to assess their potencies at specific receptor subtypes, such as the 5HT-2A serotonin receptor and the m3 muscarinic receptor. Those drugs or analogs which have selective activity at the desired receptor subtypes will provide the best candidates for treating Alzheimer's disease.

(7) Drugs that act as antagonists at the two "non-NMDA" types of glutamate receptors (i.e., kainic acid (KA) receptors, and AMPA receptors) have also been discovered by one of the Applicants (Olney) to block the toxic side effects of NMDA antagonists. Examples of such drugs which cross the blood-brain barrier include NBQX, LY 293558, LY 300164, GYKI 52466, and GYKI 53655. As with several other categories listed above, this category offers good candidates for developing relatively mild versions that would be suitable for long-term oral administration.

(8) Drugs that act as agonists at a specific type of serotonin receptor, designated as the 5HT-2A receptor, have also been recently discovered by the Applicants to block the toxic side effects of NMDA antagonists. However, it should be noted that drugs which agonize both 5HT-2A receptors and 5HT-2C receptors are usually hallucinogenic; such drugs include lysergic acid diethylamide (LSD), DOI, DOB, and DOM.

Accordingly, drugs that agonize 5HT-2A receptors, but not 5HT-2C receptors, offer good candidates for treating Alzheimer's disease. One such drug which agonizes 5HT-2A receptors while apparently having some blocking (antagonizing) effect at 5HT-2C receptors, is called lisuride. It does not cause hallucinations, and is widely used in Europe for several purposes, such as treating migraine headaches, and helping women stop lactating when it is time to stop nursing a baby.

Lisuride is also used to treat Parkinson's disease, since it is a dopamine agonist. This activity at dopamine receptors may increase the likelihood of unwanted side effects, in some patients. Accordingly, the Applicants have commenced an effort to analyze different stereoisomers of lisuride; they suspect that one stereoisomer may be substantially less active at dopamine receptors than the other stereoisomer, without losing its efficacy at 5HT-2A receptors. If that turns out to be the case, then that isomer would offer a preferred candidate for evaluation to treat Alzheimer's disease.

In addition, now that a potentially very valuable use has been disclosed for a 5HT-2A agonist drug which does not have unwanted activity at other receptors, it is likely that analogs of lisuride can be developed which have the desired selective activity at 5HT-2A receptors without having substantial activity at any other receptors. It is also likely that one or more pharmaceutical companies have already synthesized and identified other, entirely different molecules which have a desired selective agonist activity at 5HT-2A receptors without having substantial activity at any other neuronal receptors. Now that an important utility for such molecules has been disclosed herein, such drugs can be evaluated for use in treating Alzheimer patients.

Long-Term Use of Treatment Drugs

It is believed by the Applicants that the treatments disclosed herein, if properly used, can block the progressive neural degeneration that characterize Alzheimer's disease. Accordingly, although short-term administration may be useful and therapeutic and may provide a respite from the ongoing damage, it is presumed that in most patients, these treatments will need to be administered over a prolonged span of time, and presumably for the entire remaining life of a patient, to prevent or reduce a chronic NR/hypo threat to target neurons which remain viable but vulnerable, inside the brain, after one or more protective inhibitory mechanisms have been "burned out" and are no longer capable of protecting the target neurons.

The drug treatments described herein involve neuroactive drugs, most of which have various side effects. Accordingly, these treatment regimens presumably will be administered only when prescribed by a doctor, who will evaluate each patient individually and determine which drug(s) are likely to provide the best combination of effective protection and minimal side effects which can be most easily tolerated by that patient.

A number of different types of drugs, listed and discussed below, can be used to protect pyramidal and other vulnerable target neurons in Alzheimer's disease. It is anticipated that, out of this array of choices, different drugs will be preferred by different patients, due to variations in side effects coupled with a particular patient's medical condition and preferences. As an example, drugs that cause a sedating or analgesic effect which might distract and annoy some patients, may be welcomed by other patients who tend to suffer insomnia or who need a mild painkiller for a chronic condition such as arthritis.

It is also anticipated that the drugs prescribed for a particular patient can be changed periodically, to reduce the likelihood that any particular transmitter-receptor system will develop a tolerance-type problem, in which the efficacy of that drug gradually decreases. This is especially true in view of the very slow and gradual changes that characterize Alzheimer's disease; if a certain drug is (or gradually becomes) inadequate to protect pyramidal neurons against Alzheimer's disease, it may take years for a prescribing physician to recognize and diagnose that fact, and by the time the diagnosis is made, any damage suffered during the interim is likely to be permanent and irreversible.

For this same general reason, and to minimize unwanted side effects caused by substantial disruption of any specific transmitter-and-receptor pathway, it is also anticipated that physicians may decide to administer combinations of two or more drugs as disclosed herein. If two (or more) drugs as described herein can function in a cooperative and synergistic manner in the brain to protect the target neurons, the dosage of each drug can be kept as low as possible. This can minimize the problem of drug tolerance or other side effects that might be caused by higher doses of any given drug, and it may provide a more effective protection of target neurons than either drug by itself can provide.

The optimal dosage of a specific drug, for a specific patient, will need to be determined on an individual basis, by a physician who has examined that patient and who is aware of any side effects that candidate drugs or drug combinations are likely to cause in that specific patient. In general, most of the drugs described below are currently available to the public, by prescription (this excludes NMDA antagonist drugs, which generally are not approved for use in humans, and are used only for tests on lab animals). Accordingly, suitable human dosage ranges for all such treatment drugs are known, and are published in sources such as the *Physician's Desk Reference* and in manufacturer's labelling information which accompanies packages of that drug.

In general, in order to provide maximum safe levels of protection, if only a single drug is prescribed, then in the absence of indications to the contrary, the preferred daily dosage for a specific patient should generally be slightly below the largest daily dosage that can be tolerated by that patient without undue side effects. In most cases, this should provide an effective level of protection without undue risk of drug tolerance or side effects.

It should be noted that the tolerability of any side effect must always be considered in light of the alternatives. Alzheimer's disease is an utterly devastating neurological disease; it literally destroys the mind, and can render victims totally incapable of recognizing their own children, functioning competently in the world, or holding an intelligible conversation with anyone. With that as the alternative, even relatively severe side effects may be tolerable for many patients. By way of analogy, no one would ever choose to lose a leg or an arm, in an accident. But if someone has lost a leg or an arm, then the only course open to him, other than abject surrender or unending anger, is to learn to live with that loss in the most productive manner possible, and go on with whatever he has left. Accordingly, the severity of the various side effects caused by the safener drugs discussed herein will need to be resolved by each patient, individually, in consultation with his or her physician and family.

More information can be gathered on the preferred dosage range for specific treatment drugs, by means of animal tests to determine the daily dosage of that drug which is needed to protect pyramidal neurons against damage by long-term, chronic, low-level administration of a mild or moderately potent NMDA antagonist drug. Various such mild or moderate NMDA antagonist drugs are listed in the Background section; in general, these drugs act at the glutamate binding site, the glycine binding site, or the polyamine binding site, in the NMDA receptor complex. By contrast, drugs such as PCP or MK-801, which occupy the phencyclidine binding site, are much more aggressive. They can be used to provide rapid and rigorous tests of protective efficacy; in addition, they presumably can be used to evaluate long-term protective efficacy of the treatment drugs discussed herein, if used in sufficiently low dosages.

If two or more drugs are prescribed in combination, the preferred daily dosage for each drug should be reduced by a factor that can be determined by means of animal testing. Such testing can assess the efficacy of that drug combination in protecting against neurotoxic side effects caused by long-term low-level administration of an NMDA antagonist, as described above.

It should also be noted that, while the treatments described herein are intended to reduce or retard the ongoing and future neuronal damage that occurs in Alzheimer's disease, these treatments are not believed to be directly capable of restoring already-damaged or dead neurons. However, they may help Alzheimer's patients gain a respite from the continuing onslaught of neuronal damage and decay, and in some patients, this respite may allow a substantial degree of recovery and improvement, due to relearning processes and other factors.

Prior Use of Various Drugs as Palliative or Coincidental Treatments

It should be recognized that a wide variety of drugs (including virtually every known tranquilizer, sedative, sleeping pill, anti-cholinergic, alpha-2-adrenergic agonists, etc.) have been prescribed to Alzheimer patients, as palliative measures, or for the purpose of treating some other disorder that an Alzheimer patient was also suffering from. For example, some Alzheimer patients also suffer from Parkinson's disease, and in prior years a routine treatment for Parkinson's disease was an anti-cholinergic drug. It is also exceedingly common for elderly patients, including those with Alzheimer's disease, to have hypertension, which is often treated with an alpha-2-adrenergic drug such as clonidine. However, in these examples of prior drug use, the doctor is prescribing the drug for a coincidental purpose, and not with the intention or belief that it can prevent the neurodegenerative process associated with Alzheimer's disease.

The term "palliative" indicates that many drugs administered to patients with Alzheimer's disease have not been used to actually treat (by reducing, retarding, or preventing) the progressive neurodegenerative damage caused by Alzheimer's disease. Instead, they merely help patients tolerate certain symptoms such as anxiety and agitation. For example, diazepam (VALIUM) has been widely prescribed to Alzheimer patients, to help them relax and feel better about life, even as their brains are being destroyed by the disease. To the best of the Applicants' knowledge and belief, diazepam has never been prescribed (or recognized) as a drug which can, if properly administered, actually slow down and reduce or prevent the progressive degeneration that is occurring inside the brain of an Alzheimer patient.

Indeed, any medical text or treatise on Alzheimer's disease teaches that there are no known methods of suppressing or preventing the neuronal degeneration and cognitive deterioration that occurs in Alzheimer's disease, with the singular exception of tacrine, a cholinesterase inhibitor drug which was recently approved by FDA on the basis of equivocal evidence that it might transiently slow down the progression of the disease to a slight degree. None of the safener agents proposed herein as effective treatments for Alzheimer's disease are classified as cholinesterase inhibitors, or are thought to possess any significant cholinesterase inhibitor activity.

It should also be noted that the modern medical practice is to curtail the use of tranquilizers, anti-cholinergics, or other comparable drugs in Alzheimer patients, because of the potential side effects if the dose is not carefully regulated. Such drugs, if not carefully regulated, run a risk of making an Alzheimer patient feel dazed and drugged and may impair motor control, thereby increasing the risk of broken bones and other injuries due to falls and accidents. Since patients with Alzheimer's disease are not capable of regulating their own medications, and since many of these patients cannot be constantly and closely supervised by family members, nursing home administrators, or community service personnel, this can be a real problem.

Modes of Administration

Most of the drugs disclosed herein are currently used for human treatment (although some of these drugs, such as lisuride, are not currently approved in the United States, and are used only in other countries). Accordingly, suitable modes of administration are already known to physicians qualified to prescribe these drugs for Alzheimer patients.

The compositions of this invention may be administered by any suitable route which will introduce the intended drug(s) into the bloodstream. Since prolonged use is anticipated, presumably for the entire remaining life of the patient, oral administration will be preferred for most patients. Preferred modes for oral ingestion include tablets, capsules, and liquids which are swallowed, as well as transmembrane oral routes, such as lozenges, sublingual tablets or wafers, or chewing gum. Such preparations are all well known in the pharmaceutical arts, and generally include (in addition to the active agent) various types of carriers, diluents, and binders which can be molded or compressed into tablets, enclosed in gelatin capsules, mixed or suspended in a liquid syrup or emulsion, etc. Such compositions are preferably formulated or packaged in a unit dosage form, which refers to physically discrete units such as capsules or tablets, each unit containing a predetermined quantity of active material or materials calculated to produce the desired therapeutic effect, in association with a pharmaceutical carrier, such as a binding agent for compressed tablets or a liquid vehicle for syrups.

The preferred dosage of a chosen drug will depend upon both the potency of the drug and the status of the patient. As noted above, these drugs are all well known for human usage, and they will need to be prescribed by a treating physician, who will take into account any relevant factors, such as the age and weight of the patient, the severity of the patient's symptoms, and the chosen route of administration.

For Alzheimer's patients who cannot be relied upon to consistently take oral medications, other options are available. For example, depending on a patient's preferences and mental and medical condition, transdermal or other transmembrane routes (such as skin patches, permeating lotions or ointments, nasal sprays, etc.) and rectal suppositories may be useful, and subcutaneous implantation of slow-release devices (such as osmotic mini-pumps, or slowly-dissolving molded solids) may also be useful.

In addition to any other relevant criteria, including the general criteria of pharmacological acceptability, any drug which is used as described herein must be capable of permeating a mammalian blood-brain barrier (BBB) in sufficient quantities to be useful as a neuroprotective agent inside the brain. The relevant receptor activities all occur inside CNS tissue, in extracellular fluids that are isolated from circulating blood by the BBB.

For countries that do not allow patent coverage of medical treatments, on the asserted ground that such treatments are humanitarian rather than industrial, it should be noted that this invention has industrial utility, in allowing the industrial preparation and sale of medicaments for treating Alzheimer's disease.

Several of the claims list certain specific known drugs (such as clozapine, olanzapine, fluperlapine, ibogaine, and eliprodil) and then refer to "salts, isomers, and analogs thereof" which have certain specified receptor activities and which are effective in preventing NMDA receptor hypofunction from causing vacuole formation in posterior cingulate-retrosplenial neurons when administered to laboratory animals. The terms salt, isomer, and analog are used in their conventional pharmacological sense.

The term "salts" can include alkali metal salts as well as addition salts of free acids or free bases. Examples of acids which may be employed to form pharmaceutically acceptable acid addition salts include inorganic acids such as hydrochloric acid, sulfuric acid and phosphoric acid, and organic acids such as maleic acid, succinic acid and citric acid. Alkali metal salts or alkaline earth metal salts might include, for example, sodium, potassium, calcium or magnesium salts. All of these salts may be prepared by conventional means. The nature of the salt is not critical, provided that it is non-toxic and does not substantially interfere with the desired activity.

The term "isomer" as used herein includes regular chemical isomers as well as purified stereoisomers, in which certain pendant groups are coupled to a chiral carbon atom in a certain spatial configuration, to give the resulting molecule either a dextrorotatory or levorotatory configuration. It is common that a certain stereoisomer of a known drug will have a higher level of activity at a certain receptor than the other stereoisomer.

The term "analog" is used herein to refer to a molecule that structurally resembles a referent molecule (such as ibogaine, or eliprodil, as two examples), but which has been modified in a targeted and controlled manner, by replacing a specific substituent of the referent molecule with an alternate substituent, such as a methyl or ethyl group, a hydroxyl group, etc. Such substituents are limited to groups having relatively low molecular weights, such as alkyl or aryl groups, nitrogen-containing moieties such as amine groups, etc. The term "analogs" does not include bifunctional conjugates, in which a first molecular structure having a first pharmaceutical activity is coupled to a second molecular structure having a second and different pharmaceutical activity, to provide a combined molecule having both activities. Instead, analogs are limited to molecular structures that have been slightly modified (often called "tweaked") to provide an improvement in a known and desired pharmacological activity. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

Overview of Examples

In the Examples, below, a large amount of complex data is presented. The following narrative is offered in an effort to help place these data into proper context and perspective.

Example 1 contains evidence that induction of the NR/hypo state in the rat brain by administration of NMDA antagonist drugs causes widespread histopathological changes of a type and pattern extremely similar to the neurodegeneration characteristically found in the brains of humans who have Alzheimer's disease. This evidence firmly establishes the relevance of the NR/hypo mechanism to the disease process in Alzheimer's disease. Therefore, the generation of this evidence by the Applicants represents a major breakthrough in Alzheimer research, and it comes at a time when other Alzheimer researchers either have no familiarity with the NR/hypo mechanism, or are operating under the assumption that it has no relevance to Alzheimer's disease.

Initially, the Applicants found it difficult to perform a detailed analysis of the full pattern and type of damage that can be induced in the adult rat brain by treatment with an NMDA antagonist because of technical problems that had to be overcome. Therefore, the Applicants tried several approaches. For example, it had been claimed (Ellison 1994) that when PCP is infused continuously in adult rats for five days, by a subcutaneously implanted minipump, it causes injury to nerve cells in several brain regions. However, the Applicants attempted to replicate Ellison's experiments, and found that administering exactly the same dose of PCP by the same minipump method, for the same amount of time, produced no neuronal damage at all.

The Applicants also attempted to produce a widespread pattern of damage by treating rats with a single high dose of PCP, which they had previously shown would kill neurons in the PC/RS cortex (Fix et al., 1993). However, they found (Corso et al 1994) that even when a near lethal dose (50–80 mg/kg sc) was administered, a fully developed widespread pattern of damage could only be induced in a very small percentage of treated animals. For example, out of 40 rats treated by the Applicants with a very high dose of PCP (50 mg/kg i.p.), only 1 rat had a full pattern of damage.

It should be kept in mind that in order to study the brain damage syndromes that are of interest herein, in detail, it is necessary to evaluate the damage at various post-treatment intervals, and to apply several different histological methods, each of which requires its own special way of preparing the brain. Therefore, many different brains, each having a full pattern of damage, are required to perform such a study.

To resolve this problem, the Applicants took advantage of a previous observation they had made (Olney et al 1991), that excessive activation of muscarinic cholinergic receptors plays a key role in the neurotoxic mechanism by which NMDA antagonists damage the brain. It was reasoned that in the Alzheimer brain, the NR/hypo mechanism is operative over a period of years, during which cholinergic receptors might become increasingly involved. Therefore, in order to reproduce in the rat brain the same kind of pathological condition that exists in the Alzheimer brain, the Applicants decided that when treating the rats with an NMDA antagonist drug, phencyclidine (PCP), they would supplement the NMDA antagonist drug with a relatively small quantity of a muscarinic agonist, pilocarpine.

By itself, pilocarpine does not and cannot cause the type of damage observed in these tests, even if administered at very high dosages. However, when a small dose of pilocarpine (10 mg/kg i.p.) was combined with a high dose of PCP (50 mg/kg i.p.) it reliably and consistently produced severe levels of NR/hypo-induced damage, thereby allowing the Applicants to perform a detailed analysis of the full pattern of damage that the NR/hypo mechanism is capable of producing (comparable in degree of severity to the devastating damage that evolves in the Alzheimer brain over a period of years). Using this approach, the Applicants were able to make a number of critical observations pertaining to features of NR/hypo-mediated neurodegeneration that closely resemble the neurodegenerative process in humans suffering from Alzheimer's disease.

Accordingly, as described in Example 1, the Applicants established that the NR/hypo mechanism, induced by an NMDA antagonist drug supplemented by a small quantity of a muscarinic agonist, caused each of the following neurological manifestations, in a manner which duplicates the comparable manifestations that are seen in the brains of Alzheimer's disease patients when examined at autopsy:

1) a loss of synaptic complexes;
2) massive loss of neurons, with the pattern of neuronal loss duplicating the pattern typically seen in Alzheimer's disease;
3) specific cytoskeletal deformities resembling neurofibrillary tangles;
4) abnormal expression of a specific type of heat shock protein (72 kilodalton molecular weight), which is also expressed by dying neurons in the Alzheimer brain.

In summary, the Applicants found that the NR/hypo mechanism reproduces in animal brain every major characteristic feature of the neuropathology of Alzheimer's disease, except for one feature.

The single feature of Alzheimer pathology that was not reproduced in the brains of animals treated with PCP/pilocarpine was amyloid plaque formation. Absence of amyloid plaque formation does not argue against, but rather argues in favor of the Applicants' position which holds that amyloid pathology in the Alzheimer brain is the result of a genetic predisposition to which Alzheimer's disease patients are subject but laboratory rats are not. Therefore amyloid plaques would be the singular major feature of Alzheimer's disease that would not be expected to be reproduced in the animal model. The fact that the NR/hypo mechanism reproduced all of the other devastating neurodegenerative characteristics of Alzheimer's disease, in the absence of amyloid plaque formation, supports the conclusion that NR/hypo per se is a sufficient mechanism to cause the severe neurodegenerative changes in Alzheimer's disease, and amyloid plaque formation may be important only in its ability to promote and increase the degree of severity of the NR/hypo process.

Examples 2, 3 and 4 pertain to the role of the cholinergic muscarinic transmitter system in producing the neuropathological manifestations of Alzheimer's disease.

Example 2 pertains specifically to the role of the m3 muscarinic receptor subtype in producing "neurofibrillary tangles" (abbreviated as NFT's), which are a hallmark manifestation of the neuropathology seen in the Alzheimer brain. NFT are corkscrew-like deformities that occur in the cell body and dendritic processes of the neuron in Alzheimer's disease. It is on the surface of the cell body and dendritic processes that most of the transmitter receptors are located through which the nerve cell receives incoming messages. The fact that NFTs are localized to these portions of the neuron that receive synaptic inputs suggests that these synaptic inputs may have something to do with NFT formation. NFTs are an important feature of the neuropathology of Alzheimer's disease in that they occur as an antecedent to cell death in the specific neurons that degenerate unto death in the Alzheimer brain.

It is generally believed that the NFT corkscrew deformity in the Alzheimer brain is caused by excessive phosphorylation of a protein known as "tau". The tau protein is associated with microtubules that comprise an important component of the cytoskeleton (these relatively stiff intracellular tubules cause neurons to adopt and maintain a certain shape). When tau protein becomes hyperphosphorylated, it causes filaments associated with the microtubules in the cytoskeleton to become twisted. When this tube-twisting process becomes severe, it gives a dendrite a contorted, corkscrew-like configuration.

Phosphorylation of proteins is an enzyme-driven process, and one of the major enzymes that performs this function is protein kinase C. Protein kinase C is coupled to the muscarinic cholinergic transmitter system, such that when specific muscarinic receptors (m1 or m3) are stimulated, this activates protein kinase C and promotes protein phosphorylation. Therefore, a toxic process by which m1 or m3 muscarinic receptors are hyperstimulated represents a possible mechanism that could cause hyperphosphorylation of the tau protein, and lead to NFT formation.

The Applicants have shown that muscarinic antagonists block the NR/hypo brain damage induced by NMDA antagonist drugs. This signifies that hyperactivation of a muscarinic receptor is involved in mediating NR/hypo-induced brain damage. However, since all muscarinic antagonists interact with multiple muscarinic receptor subtypes, merely demonstrating that muscarinic antagonists block NR/hypo brain damage does not establish which muscarinic receptor subtype is involved. In order to link the NR/hypo mechanism to the pathological process by which NFT are formed, it would be necessary to show that the muscarinic receptor subtype that is hyperactivated in the NR/hypo brain damage syndrome is either an m1 or m3 receptor.

In Example 2 evidence is presented that documents that the muscarinic receptor subtype that is hyperactivated in the NR/hypo brain damage syndrome is an m3 receptor This conclusion is supported by experiments in which the Applicants studied a large number of muscarinic antagonists and found that they have a certain order of potencies for preventing the neurotoxic side effects of the powerful NMDA antagonist, MK-801. When the order of potencies of these muscarinic antagonists for preventing the neurotoxic effects of MK-801 was compared with the order of binding affinities of these same muscarinic antagonists to each of the five known muscarinic receptor subtypes (m1, m2, m3, m4 and m5), it was found that the order of potencies matched the order of binding affinities for the m1 and m3 receptors better than for the other three receptor subtypes, and the match was particularly good for the m3 receptor. It follows that m1 or m3 receptors are most likely the muscarinic receptor subtypes through which NR/hypo brain damage is mediated.

Example 3 addresses the question whether the muscarinic cholinergic transmitter system is truly hyperactive in Alzheimer's disease, as the Applicants assert, or is hypoactive, as traditional thinking in Alzheimer research apparently assumes. One reason that other Alzheimer researchers assume that the muscarinic system is hypoactive in Alzheimer's is that tacrine, the only drug currently approved by FDA for the treatment of Alzheimer's disease, is believed to confer transient benefits in Alzheimer's disease by causing increased activation of critical m1 or m3 muscarinic receptors, thereby overcoming the presumed hypoactivity of these receptors. However, there is no reliable evidence establishing whether tacrine truly increases m1/m3 activity or, consistent with the Applicants' assertion, decreases it.

In Example 3, specific immunocytochemical evidence supporting the Applicants' position is presented. This evidence became available only very recently, because it depends on the use of labeled antibodies that have just recently been developed for studying the localization of each of the five muscarinic cholinergic receptor subtypes in the brain. Each antibody is coupled to a marker molecule, and the antibody/marker complex is reacted with a brain tissue slice to allow the antibody to bind to the specific protein of the muscarinic receptor against which it was developed. Thus, the antibody/marker complex will bind to and mark the location of that receptor protein, and the localization of receptor protein can then be studied by light and electron microscopy.

Using these new immunocytochemical probes, the Applicants have observed that the cholinergic neurons that are clustered in the basal forebrain and provide the main source of cholinergic innervation to neurons throughout the cerebral cortex, including neurons in the PC/RS cortex, have m2 receptor protein localized to their cell bodies in the basal forebrain. In addition, m2 receptor protein was localized to certain axon terminals in the PC/RS cortex, and m3 receptor protein was localized to the dendritic processes of PC/RS pyramidal neurons (e.g., pyramidal neuron 100 in FIG. 1).

The Applicants' interpretation of these findings is that the m2 receptor protein is found in the cell bodies of basal forebrain cholinergic neurons, because that is where the receptor protein is synthesized. It is then transported through the axonal fiber to the terminal portion of that fiber in the PC/RS cortex, where it functions as an autoreceptor that regulates (inhibits) the rate at which the axon terminal releases acetylcholine onto an m3 receptor which is on the dendrite of the PC/RS pyramidal neuron 100 in FIG. 1.

In light of this new evidence pertaining to m2 muscarinic receptors, it may be necessary to re-evaluate the basis for the clinical benefits conferred by tacrine. Like all cholinesterase inhibitors, tacrine increases the duration of action of ACh at muscarinic receptors. If it increased the duration of action of ACh at m2 autoreceptors which inhibit the release of ACh at m3 receptors on PC/RS neurons, this will decrease the amount of ACh released at the m3 receptors, and it will correspondingly decrease the activity of these receptors. The Applicants' assertions and analysis herein indicate that this type of action via autoregulatory m2 receptors might, indeed, be beneficial in treating Alzheimer's disease, but the benefit may be due to a decrease, rather than increase, in activity at m3 receptors.

Example 4 provides evidence from human studies further addressing the issue whether the muscarinic transmitter system is hyperactive or hypoactive in Alzheimer's disease. A second basis for the common belief that the muscarinic system is hypofunctional in Alzheimer patients is that when the brains of Alzheimer patients are autopsied, it is found that in the basal forebrain, where the cell bodies of cholinergic neurons are densely clustered, many of these neurons are missing. They have degenerated, but the muscarinic receptors in the cerebral cortex are still there. This has caused many Alzheimer researchers to assume that the cholinergic neuronal system is wiped out from the beginning, and this leaves the receptors without innervation, from which it follows that drugs are needed to reactivate these receptors.

However, a flaw in this reasoning is that it is based on examination of Alzheimer brains in the very latest stages of the disease. The Applicants assert herein that the cholinergic system is intact early in the disease, and both the cholinergic system and non-NMDA glutamate receptor systems (kainic acid receptors, and AMPA receptors) are hyperactive, and it is this hyperactivity (secondary to the NR/hypo disinhibitory mechanism) that damages and eventually destroys many neurons throughout the brain.

Example 4 presents two lines of evidence, both from human studies, that support the Applicants' position. The first line of evidence was generated by the Applicants in collaboration with Dr. Daniel McKeel, MD, a pathologist who is Director of a brain tissue bank maintained by the Washington University (St. Louis) Alzheimer's Disease Research Center (ADRC). The ADRC brain bank contains the brains of many deceased Alzheimer's disease patients, and these brains are categorized according to the clinical stage of illness at the time of death. Many brains are available from Alzheimer's disease patients who died in the late stages of the illness and a small number are available from patients who died in the very early stages.

In collaboration with Dr. McKeel, the Applicants have made the preliminary observation that in a small number of patients who died in the early stages of the disease, basal forebrain cholinergic neurons appear to be well preserved, whereas in patients who died in the very late stages cholinergic neuronal loss is striking. These findings have not been published or publicly communicated. The Applicants and Dr. McKeel intend to expand the study to include a larger number of Alzheimer brains in both early and late stages of the illness and will report the findings when this goal is achieved. On the basis of these preliminary findings it appears that in the early stages of Alzheimer's disease the cholinergic muscarinic transmitter system is intact and viable, contrary to the assumptions of most Alzheimer's disease researchers that it is defunct and hypoactive. These findings strongly support the Applicants' assertion that the cholinergic system is intact early in Alzheimer's disease and does not degenerate until late in the disease after cholinergic neurons have contributed to the death of many other neurons.

In Example 4, a second line of evidence is presented as follows. In recent years, new methods have been developed for non-invasively imaging the brains of Alzheimer's disease patients who are still alive. One such method, magnetic resonance spectroscopy, provides for the use of tracer molecules that reveal the status of certain neuronal systems and neurochemical processes in the living brain. For example, it is possible to evaluate the status of the cholinergic neurons, using choline as a tracer, and to evaluate the status of other neurons using n-acetyl-aspartyl-glutamate as a tracer.

A recent study using these methods (Ross et al 1993) reported that early in the course of Alzheimer's disease, the cholinergic neurons appeared to be intact, while substantial evidence for loss of other neurons was discernible. In addition, Ross et al noted that in early-stage Alzheimer's disease, the phosphoinositide second messenger system that is coupled to m3 cholinergic receptors appeared to be accumulating excessive amounts of certain metabolites. Although some other researchers have suggested that this finding indicates that there may be a slowing down or impedance in metabolic pathways associated with cholinergic receptors (consistent with the conventional belief that the cholinergic system is hypoactive in Alzheimer's disease), a more likely interpretation would be that the cholinergic system is overly active (consistent with the Applicants' assertions herein).

In Example 5, the Applicants present evidence that addresses a fundamental principle that is important for understanding how an NR/hypo mechanism might be instilled in the Alzheimer brain. This is a simple but subtle and rather paradoxical principle that often is not adequately grasped even by researchers who are familiar with excitotoxicology concepts. The paradox is that the formula for instilling an NMDA receptor hypofunctional state in the brain is to begin with an NMDA receptor hyperfunctional state.

In Example 5, the Applicants focus on a neuroendocrine regulatory system in the hypothalamic region of the brain, and show what happens to that system when the NMDA receptors in that system are experimentally hyperactivated. What happens is that the NMDA receptors in this hypothalamic system are "burned out" and destroyed by an excitotoxic mechanism which, in at least some cases, also destroys the NMDA receptor-bearing neurons. Even if the neurons are not destroyed, the NMDA receptors are destroyed. This leaves this hypothalamic brain region deficient in NMDA receptors, i.e., it is in an NR/hypo state.

The Applicants show that when an NR/hypo state is created in the hypothalamus, the hypothalamus loses its ability to regulate reproductive hormones. This becomes a disease state that causes a number of abnormalities, including obesity, infertility, and ongoing degeneration of reproductive organs. This example of an experimentally-induced disease state is offered as an analogy to what happens spontaneously in the Alzheimer brain. Beta amyloid accumulation renders NMDA receptors hypersensitive to glutamate; this in turn causes damage to the NMDA receptor system, which then results in an NR/hypo state. This condition then functions as a disease mechanism to cause further neurodegeneration and cognitive disturbances, as symptomatic manifestations of the NR/hypo disease process.

In Example 6, evidence is cited that beta amyloid, an abnormal protein that accumulates in Alzheimer brains because of a genetic predisposition, interacts with NMDA receptors to make these receptors hypersensitive to endogenous glutamate. This represents a mechanism by which hyperactivation of NMDA receptors in the Alzheimer brain may result in destruction of certain NMDA receptor-bearing neurons (e.g., GABAergic neurons 20, 30 and 40 in FIG. 1). The resulting loss of these neurons and their NMDA receptors will produce an NR/hypo state within the circuit depicted in FIG. 1.

As the Applicants have shown in Example 1, when an NR/hypo state is induced in this circuit, it results in widespread degeneration of neurons and in various other histopathological changes characteristic of Alzheimer's disease. Thus, in Example 5 the Applicants have shown how an NR/hypo disease state can be created by experimentally hyperactivating NMDA receptors in the rat brain, and in Example 6 they have cited evidence for an analogous situation in which an NR/hypo disease state can develop spontaneously in the human Alzheimer brain, as a result of a genetic predisposition to accumulate beta amyloid, which can spontaneously trigger an NMDA receptor hyperactivation syndrome, which in turn gives rise to an NR/hypo disease state that is capable of producing all of the neuropathological signs and symptoms of Alzheimer's disease.

In Example 7, the Applicants cite evidence from a number of laboratories. This evidence establishes that in the normal aging brain of both rodents and primates, there are unknown mechanisms that cause the NMDA receptor system to become progressively hypofunctional with advancing age. The significance of this observation is as follows: although the moderately severe degree of NR/hypo that develops in the "normal" aging brain is not sufficient in itself to trigger widespread neuronal degeneration, the evidence presented in Example 1 signifies that the NR/hypo mechanism, by itself, may be capable of triggering widespread neurodegeneration, if the degree of NR/hypo is severe enough. Thus, the only difference between the "normal" aging brain and the Alzheimer brain appears to be this: in the Alzheimer brain, an auxiliary mechanism (beta amyloid accumulation) is operative, which increases the severity of NR/hypo beyond a critical threshold. After crossing that threshold, it begins to trigger widespread and devastating neurodegeneration.

Example 8 describes screening assays that were used to evaluate the potency of NMDA antagonists. It evaluates the ability of candidate drugs to protect against excitotoxic lesions that are caused in CNS tissue by N-methyl-D-aspartate (the probe drug for which NMDA receptors were named). NMDA is a convulsant drug that powerfully stimulates neurons, causing hyper-excitation; it can cause cell necrosis and death within a few hours, unless NMDA receptors are protected against this convulsant drug.

The assays in Example 8 allow candidate NMDA antagonist drugs to be quantified and ranked for potency in blocking NMDA receptors, using a uniform and consistent set of tests. All of the NMDA antagonist drugs tested by the Applicants in these assays had previously been reported as NMDA antagonists, by other researchers. Accordingly, the results from these particular assays should be regarded as confirmatory, rather than new discoveries. Among other things, they confirmed that the Applicants had obtained a good sample of each drug, and they provided the Applicants with potency data, obtained from a uniform, consistent set of assays.

These in vitro assays use pieces of retinal tissue, from chicks; this provides a simple, inexpensive model which has been found suitable for this particular assay. Chick tissue provides a better model of adult mammalian neurons than embryonic or juvenile mammalian tissue. Unlike newborn mammals, which are usually blind at birth because their retinal neurons are not yet fully developed, baby chicks can see quite well as soon as they emerge from the shell, and the NMDA receptors in their retinas are fully mature and functional.

Example 8 describes screening assays that were used to evaluate the potency of NMDA antagonists. It evaluates the ability of candidate drugs to protect against excitotoxic lesions that are caused in CNS tissue by N-methyl-D-aspartate (the probe drug for which NMDA receptors were named). NMDA is a convulsant drug that powerfully stimulates neurons, causing hyper-excitation; it can cause cell necrosis and death within a few hours, unless NMDA receptors are protected against this convulsant drug.

The assays in Example 8 allow candidate NMDA antagonist drugs to be quantified and ranked for potency in blocking NMDA receptors, using a uniform and consistent set of tests. All of the NMDA antagonist drugs tested by the Applicants in these assays had previously been reported as NMDA antagonists, by other researchers. Accordingly, the results from these particular assays should be regarded as confirmatory, rather than new discoveries. Among other things, they confirmed that the Applicants had obtained a good sample of each drug, and they provided the Applicants with potency data obtained from a uniform, consistent set of assays.

These in vitro assays use pieces of retinal tissue, from chicks; this provides a simple, inexpensive model which has been found suitable for this particular assay. Chick tissue provides a better model of adult mammalian neurons than embryonic or juvenile mammalian tissue. Unlike newborn mammals, which are usually blind at birth because their retinal neurons are not yet fully developed, baby chicks can see quite well as soon as they emerge from the shell, and the NMDA receptors in their retinas are fully mature and functional.

The drugs that were tested by the Applicants in these retinal tissue assays can be divided into various categories, as follows:

(1) Competitive NMDA antagonists, which block NMDA receptors by action at the glutamate binding site. These drugs include CPP, CPP-ene, and CGS 19755.

(2) Non-competitive NMDA antagonists which block NMDA receptors by action at a glycine binding site. Such drugs include kynurenic acid, 7-chloro-kynurenic acid, and three drugs (referred to as CNQX, DNQX, and NBQX) that belong in the quinoxalinedione family of compounds, discussed below. Other glycine site blockers that were not tested by the Applicants, but which have been reported by others, include R(+)-HA-966, 5,7-dichlorokynurenic acid, 5-iodo-7-chloro-kynurenic acid, and certain other quinoxalinediones, including ACEA-1021 and ACEA-1031.

(3) Non-competitive NMDA antagonists that block NMDA receptors by action at the polyamine binding site. Agents tested by the Applicants that fit into this category include ifenprodil, and eliprodil (also called SL-82.0715).

(4) Non-competitive NMDA antagonists that block NMDA receptors by action at the PCP binding site. Many agents tested by the Applicants fit into this category, including MK-801, PCP, ketamine, tiletamine, dextromethorphan, dextrorphan, memantine and ibogaine.

The average potencies of these various types of NMDA antagonists, as indicated by the chick retina assays, are listed in Table 1, in Example 8.

These and other known NMDA antagonists (such as MDL-28,469, MDL-100,748, MDL-29,951, L-689,560, L-687,414, ACPC, ACPCM, ACPCE, arcaine, diethylenetriamine, 1,10-diaminodecane, and 1,12-diaminododecane) are discussed and fully identified by chemical structure in various publications (e.g., Carter et al 1988, Rogawski 1992, Massieu et al 1993, Keana et al 1995, Warner et al 1995, and other articles cited therein).

The family of drugs known as quinoxalinediones deserve special attention as NMDA antagonists, because they offer some of the most interesting and potentially promising agents being studied today. These agents have generated major interest among certain pharmaceutical companies, because they can suppress activity both at NMDA receptors (by acting at the glycine binding site), and at non-NMDA glutamate receptors (i.e., kainic acid receptors, and AMPA receptors). Certain quinoxalinediones have even been developed (by different companies) with different preferential affinities for NMDA versus non-NMDA receptors.

At one end of the dual-affinity spectrum is a quinoxalinedione called NBQX (the full name is 2,3-dihydroxy-6-nitro-7-sulfamoyl-benzo(F)quinoxaline; see Sheardown et al 1990, and PCT application WO-92/11012, invented by T. Klockgether et al, assigned to Schering Berlin & Bergkamen AG). It has a relatively strong binding affinity for non-NMDA receptors, and a somewhat weaker affinity for the glycine site at NMDA receptors. NBQX does not cause vacuoles, despite its NMDA antagonist activity; indeed, because of its ability to suppress activity at non-NMDA glutamate receptors, it can even act as a safener agent, to prevent potent NMDA antagonists from causing vacuoles. This activity is described in Example 11.

At the other end of the dual-affinity spectrum, two quinoxalinediones called ACEA 1021 and ACEA 1031 (Warner et al 1995; Keana et al 1995) reportedly exert stronger blocking activity at NMDA receptors than at non-NMDA receptors. Presumably, these agents can act as relatively potent and effective NMDA antagonists which also have an inherent safener activity, due to their actions in suppressing non-NMDA glutamate receptors.

As of this writing, the Applicants had not yet obtained or tested either of the ACEA compounds; however, it is believed that at least one pharmaceutical corporation has abandoned its efforts to develop or commercialize other NMDA antagonists, so it can concentrate on the ACEA compounds as its primary candidates for more research. In Light of the new disclosures herein by the Applicants, those compounds and their analogs should be regarded as good candidates for treating Alzheimer's disease during the presymptomatic stages (i.e., so long as an NR/hypo condition does not exist inside the patient's brain).

In addition, the fact that NBQX and the ACEA compounds belong in the same chemical class (quinoxalinediones) suggests that other members of this class can be developed which have other desired balance points, such as roughly equal affinities for both the glycine NMDA receptor site and for non-NMDA receptors.

Example 9 describes screening assays that were used to quantify the toxic side effects that were caused by the various NMDA antagonist drugs tested by the Applicants. In these assays, adult rats were injected with varying doses of an NMDA antagonist. After several hours, the animal was sacrificed, and a carefully selected area from its brain was analyzed microscopically, to determine whether it caused the cellular vacuoles that are caused by most NMDA antagonists.

Any NMDA antagonist drugs that induce vacuoles in lab animals (or which cause hallucinations, when tested in humans) should be accompanied by a safener drug, as described herein. However, it should be noted that two NMDA antagonist drugs did not cause any detectable vacuole reaction in the test conditions that were used. Those drugs were eliprodil and ibogaine.

Example 10 describes assays on those two drugs, showing that if these drugs were co-administered with a selective sigma agonist, they caused a vacuole reaction. These results indicated that the inherent safening activity of these two NMDA antagonists apparently is due to blocking activity at sigma receptors.

Example 11 describes assays on NBQX (a quinoxalinedione, as discussed above) to confirm that it is a safener agent which can reduce the toxic side effects of MK-801. NBQX is difficult to work with, because of certain pharmacokinetic factors; apparently, it penetrates the BBB in substantial quantities, but there appears to be a cell or tissue response which causes NBQX to be ejected from the brain fairly rapidly, and it does not sustain desirable concentrations inside the brain. Those problems led to both (a) systemic tests, using intraperitoneal injections every half hour for a total of four injections, and (b) microinjection of NBQX directly into brain tissue. In both sets of tests, the results were positive (i.e., the vacuoles caused by MK-801 were substantially reduced or prevented). These tests are described in Example 11.

Example 12 describes assays on various other safening agents which can block the toxic side effects of potent NMDA antagonists. The results of these tests are provided in Table 2.

In summary, the evidence disclosed herein shows that an NR/hypo condition apparently plays a major role in the widespread neurodegeneration caused by Alzheimer's disease, and may indeed be the crucial element that leads, through various mechanisms, to essentially all of the major neurodegenerative manifestations of this disease. Accordingly, the safener drugs which can protect vulnerable corticolimbic neurons against damage induced by a drug-induced NR/hypo condition can also help protect those neurons against endogenous NR/hypo as a component of Alzheimer's disease.

EXAMPLES

Example 1

Evidence that Drug-Induced NMDA Receptor Hypofunction can Induce Neurodegeneration Patterns Identical to Alzheimer's Disease Adult female rats were injected subcutaneously with an NMDA antagonist drug, phencyclidine (PCP), at 50 milligrams of drug per kilogram of body weight (mg/kg sc), accompanied by a small dose of a muscarinic agonist, pilocarpine (10 mg/kg sc). At various times (4, 16, 24, 48, 72 and 96 hours) after treatment, the rats were anesthetized and perfused with fixative to allow their brains to be prepared for histological evaluation.

Several methods of tissue preparation were used; in general, these same methods are suitable for highlighting and clearly demonstrating the neuropathological changes that occur in the brains of patients with Alzheimer's disease. These methods include: (1) a silver impregnation stain, for demonstrating cytoskeletal deformities in degenerating neurons; (2) an immunocytochemical stain using fluorescently labelled monoclonal antibodies that bind specifically to a 72 kilodalton heat shock protein; and, (3) a hematoxylin and eosin stain, for confirming that neuronal necrosis (cell death) has occurred.

Degenerating neurons in various brain regions were also examined by electron microscopy, to obtain evidence for loss of synaptic complexes, and a computer-assisted cell plotting system was used to plot the location and count the frequency with which degenerating neurons were found in each brain region.

The conclusions and data described below are supported by a set of photographs, which provide visual confirmation and proof of what was actually observed. Since it is very difficult to print such photographs at sufficiently fine resolution in a patent, those photographs have been submitted to the U.S. Patent and Trademark Office, along with this application, as attachments to a sworn declaration signed by Prof. John Olney. Those photographs will become available for public inspection, in the file wrapper of this application, as soon as a patent issues based on this application. Those same photographs have also been submitted for publication in a refereed scientific journal, and probably will be published in late 1996 or early 1997.

The following observations relevant to Alzheimer's disease were made:

Loss of Synaptic Complexes

Loss of synaptic complexes is a major feature of the neuropathological changes in Alzheimer's disease, and is the feature that has been found to correlate most closely with memory loss and cognitive deterioration. By electron microscopy, the Applicants found that early in the NR/hypo neurodegenerative syndrome, dendritic spines (which are the neural elements where most of the synaptic complexes are located) swell massively and selectively degenerate, so that the synaptic complexes on their surfaces are destroyed. The specific patterns of damage seen in the rat brain resembled, in an apparently identical manner, the corresponding patterns that are seen in the brains of humans with Alzheimer's disease, when examined at autopsy. This provides an excellent model and explanation for this pattern of damage to, and loss of, synaptic complexes in humans with Alzheimer's disease.

Neuronal Cell Death

Massive loss of neurons throughout many neocortical and limbic brain regions is a hallmark characteristic of Alzheimer's disease. To establish that the NR/hypo mechanism results not only in cell injury but in cell death, the Applicants systematically examined the brains of rats 4 days following PCP/pilocarpine treatment. Sections prepared at 1 millimeter intervals from one side of the brain were stained, using hematoxylin and eosin; sections prepared at 1 millimeter intervals from the other side of the brain were stained using a silver impregnation stain.

The Applicants used the hematoxylin/eosin stain, because it is well established in the field of neuropathology that this stain clearly and unequivocally identifies necrotic (dead) neurons, making the cell body stand out as a brightly eosinophilic (pink) profile, while the nucleus stains dark blue and appears shrunken.

The Applicants also used the silver impregnation procedure, because this method causes the entire cell body and dendritic arbor of degenerating neurons to stain a deep brown or black, against a pale unstained background. This provides an opportunity to evaluate cytoskeletal deformities and other changes occurring throughout the entire neuron. However, without additional information, it is not clear what the uptake of silver stain by a neuron implies, with regard to reversibility or irreversibility of the degenerative process (i.e., whether cell death has occurred). Therefore, to validate the silver stain as a method for demonstrating cell death, the Applicants compared the results of this stain, on tissue sections from one side of the brain, with the results from the hematoxylin and eosin stain of tissue sections on the other side of the brain.

The Applicants observed, with the hematoxylin/eosin stain, that many neurons in many different brain regions were killed by the PCP/pilocarpine treatment. The Applicants also observed that in corresponding locations in the other half of each brain, the same neuronal populations were deeply and selectively stained by the silver stain.

These findings clearly established that the NR/hypo mechanism kills many neurons throughout many regions of the brain, in a manner that closely resembles the neuronal death found in the brains of Alzheimer patients at autopsy. Since the silver stain showed the same pattern of positive staining as shown by the hematoxylin-eosin stain, these findings validate the silver stain as a valuable method for studying the pattern and nature of this neuronal death process in its various stages of progression.

Patterns of damage

Using silver stained sections, which show the degenerating neurons as vivid silhouettes, the Applicants counted and plotted the location of the degenerating neurons at all rostro-caudal levels of the rat brain four days following PCP/pilocarpine treatment. Maps displaying the distribution of degenerating neurons at each of eight rostrocaudal (front to back) levels of the brain were prepared. When the distribution pattern shown in these maps was compared with the distribution of degenerating neurons described by various Alzheimer researchers (including Price et al 1991; Braak and Braak 1991; Brun and Englund 1981; Minoshima et al 1994; and Insausti et al 1993), it was clear that the patterns are almost identical.

Cytoskeletal deformities; neurofibrillary tangles (NFT's)

A very important feature of Alzheimer pathology is that degenerating neurons show a characteristic corkscrew-like deformity of their dendritic processes. This deformity is referred to as a neurofibrillary tangle (abbreviated as NFT). The NFT deformity is vividly displayed by certain silver staining methods, but not by most other stains such as hematoxylin-eosin stain. The frequency with which NFT are found in Alzheimer brains correlates with the severity of the illness, and with the degree of memory loss and other signs of cognitive deterioration.

Silver stained sections at every level of the rat brain in the 24 to 48 hour interval following PCP/pilocarpine treatment showed numerous degenerating neurons, all of which displayed a conspicuous corkscrew deformity. This deformity, in the drug-treated rat brains, appeared identical to the NFT corkscrew deformity that is a hallmark characteristic of degenerating neurons in the brains of Alzheimer patients.

In addition, as described in the next paragraph, the heat shock protein stain also demonstrated the same type of corkscrew deformity in degenerating neurons, after PCP/pilocarpine treatment.

Abnormal heat shock protein expression

Neurons in healthy brains do not normally express a certain type of "heat shock" protein which has a molecular weight of 72 kilodaltons (HSP-72). By contrast, neurons undergoing degeneration in Alzheimer's disease express this protein, as a response to the injurious mechanism that is causing them to degenerate (Hamos et al 1991).

It is possible to observe and display specific neurons that are expressing the HSP-72 heat shock protein, by reacting a brain tissue section with monoclonal antibodies which bind to HSP-72, and which are attached to a labelling molecule that is visible under an ordinary light microscope as a black stain. When the labelled antibody binds to HSP-72 within an injured neuron, it causes the injured neuron to become visible as a darkly stained structure.

Using brain tissue from rats that had been treated 24 hours earlier with PCP/pilocarpine, tissue sections were exposed to the labeled HSP-72 antibody. This caused neurons injured by the NR/hypo mechanism to stain darkly, signifying that the NR/hypo mechanism had caused abnormal expression of HSP-72 in these neurons. In addition, this staining process caused the neuronal dendrites of the injured neurons to show a conspicuous corkscrew deformity, similar to that observed by the silver staining approach, and similar to the neurofibrillary tangles found in humans suffering from Alzheimer's disease.

Amyloid plaques

The Applicants did not find evidence that amyloid plaque formation occurs in the brains of animals treated with PCP/pilocarpine. Absence of this amyloid abnormality does not contradict, in any way, the findings or assertions contained herein. Amyloid pathology in the brains of people suffering from Alzheimer's disease is believed to result from one or more genetic predispositions (an unfavorable apolipoprotein E isoform, or a mutation affecting amyloid precursor protein), which is a condition that Alzheimer patients are subject to, but laboratory rats are not. Therefore, amyloid plaques are the single major feature of Alzheimer's disease that would not be expected to be reproduced in an animal model, except possibly in animals that have been genetically transformed to contain the mutant genetic isoform.

Example 2

Evidence Implicating M3 Muscarinic Receptor Hyperactivity as a Key Feature of the NR/HYPO Mechanism by which Neurofibrillary Tangles are Formed One of the Applicants herein (Olney) has previously reported that various drugs which act as antagonists at muscarinic receptors can prevent the neurotoxic side effects of NMDA antagonist drugs. This signifies that hyperactivation of a muscarinic receptor is involved in mediating the neurotoxic action. However, the muscarinic antagonists that prevent the neurotoxic action of NMDA antagonists act at all 5 of the known muscarinic receptor subtypes; accordingly, this finding does not establish which receptor subtype mediates the neurotoxic reaction. It is important to clarify which receptor subtype mediates this reaction in that two muscarinic receptor subtypes (m1 and m3) are coupled to a phosphokinase C second messenger system which, through its protein phosphorylation functions, may play a key role in the formation of NFT.

In order to determine specifically which muscarinic receptor subtype mediates the neurotoxic reaction, the Applicants performed a series of tests in which various muscarinic antagonists that prevent MK-801 neurotoxicity were assigned an ED50 rating. This rating is established, for various muscarinic antagonist drugs, by treating rats with a fixed quantity of an NMDA antagonist (MK-801), and with varying dosages of various muscarinic antagonists, and by counting the number of vacuolated neurons per section in a region of the PC/RS cortex where the neurotoxic reaction is known to be the most severe. For each muscarinic antagonist drug that was tested, regression analysis was used to determine the dosage of the drug which reduced, the number of vacuolated neurons to 50% of the number that occurred in control rats that received only MK-801.

Once an ED50 value was established for each muscarinic antagonist, these agents were ranked for potency according to the relative magnitude of their ED50 values. Drugs with small ED50 numbers are very potent, since they require only a small quantity to block the toxic side effects of MK-801, while drugs that require large dosages to block MK-801's side effects are less potent and have larger ED50 values.

In a published study (Olney et al 1991), the order of potencies of these muscarinic antagonists was compared with the order of binding affinities for the two muscarinic receptor subtypes (m1 and m2) which were known at that time. It was determined that the order of potencies correlated with the order of binding affinities for the m1 but not the m2 receptor. However, during that same era, molecular biologists were successful in cloning and sequencing 5 muscarinic receptor subtypes. Bolden et al 1992 reported the transfection of cultured cells with genetic material, causing them to express these muscarinic receptor subtypes (a given cell would express only one specific subtype corresponding to the subtype-specific genetic material with which it was transfected). Bolden et al then used the transfected cells in receptor binding studies to determine the relative binding affinities of various muscarinic antagonists for each of the 5 muscarinic receptor subtypes.

When the ED50 values for each of the muscarinic antagonists (i.e., their potency in protecting against MK-801 neurotoxicity) were compared to the published values for their binding affinities for each of the muscarinic receptor subtypes, it revealed a better correlation for the m3 subtype than for any of the other four receptor subtypes. In fact, the correlation for the m3 subtype was perfect with the exception that trihexyphenydyl was more potent in blocking MK-801 neurotoxicity than would be predicted by its binding affinity to the m3 receptor. That single anomaly can be explained as follows: trihexyphenydyl has strong binding affinity not only to muscarinic receptors, but also to sigma receptors, and both of these receptor systems contribute to MK-801 neurotoxicity (FIG. 1). Its action at sigma receptors would not influence its rank order of affinity for binding to the m3 receptor, but its sigma action would add to its m3 action to increase its potency in blocking MK-801 neurotoxicity.

The first analysis implicated the m1 receptor, but the second more definitive analysis indicates that it is most likely the m3 receptor subtype that mediates (or plays the most heavily predominant role in) the NR/hypo neurotoxic reaction. Regardless whether it is the m1 or m3 receptor that has the most prominent role, either of these receptor subtypes, when hyperactivated, can excessively stimulate protein kinase C, which in turn can cause hyperphosphorylation of tau protein, and hyperphosphorylation of tau protein is believed to be an antecedent step leading to the production of neurofibrillary tangles (NFT's) in Alzheimer's disease.

Therefore, the recent findings of the Applicants, coupled with other published data on receptor affinities, show that:

(1) the drug-induced NR/hypo mechanism produces changes in animal brains that closely resemble NFT in humans suffering from Alzheimer's disease; and, (2) the NR/hypo mechanism, by causing hyperactivation of the m1 or m3 class of muscarinic receptors, produces disturbances in m1/m3-linked second messenger systems which are likely to contribute to the formation of neurofibrillary tangles in humans suffering from Alzheimer's disease.

Example 3

Immunocytochemical Evidence Corroborating M3 Muscarinic Receptor Hyperactivity as a Mechanism that Contributes to NFT Formation and Neuronal Degeneration in Alzheimer's Disease The evidence gathered by the Applicants indicates that hyperactivity of the cholinergic muscarinic transmitter system plays an important role in NFT formation and neuronal degeneration in Alzheimer's disease. This is in direct contrast to the predominant thinking in Alzheimer research, which holds that the cholinergic muscarinic transmitter system is not hyperactive, but rather is hypoactive, in Alzheimer's disease.

One reason that most Alzheimer researchers believe that the cholinergic system is hypoactive in Alzheimer's disease is that tacrine, a cholinesterase inhibitor, has been shown to be transiently beneficial in retarding the progression of symptoms in Alzheimer's disease. It is commonly believed that the reason tacrine is beneficial is that m1 and m3 cholinergic receptors are hypoactive in Alzheimer's disease and tacrine corrects this deficit by increasing cholinergic activity at these receptors. However, it has never been proven that these receptors are hypoactive in AD, nor that tacrine actually does increase cholinergic activity at these receptors. According to the Applicants' assertions herein, these receptors are hyperactive and tacrine would have to decrease their activity in order to have a beneficial effect in Alzheimer's disease. Recently, new methods became available for studying the muscarinic receptor system. In Example 3, the Applicants have applied these methods to evaluate the possibility that tacrine might decrease instead of increase cholinergic activity at m3 receptors.

Molecular biologists recently were able to clone and sequence all five of the muscarinic receptors and this provided an opportunity for other researchers to develop antibodies against each of these receptors, thereby enabling them to apply immunocytochemical methods to study the localization of all cholinergic muscarinic receptors in the brain. This method entails labelling each antibody and reacting it with a brain tissue slice to allow the labeled antibody to bind to the specific protein of the muscarinic receptor against which it was developed. Since the antibody is coupled to a label that is visible under the microscope, this provides a means of visualizing the location of the receptor protein. Methods have become available for visualizing the receptor protein at both the level of the light microscope and the electron microscope. Applying these methods, the Applicants have observed that the cholinergic neurons that are clustered in the basal forebrain and provide the main source of cholinergic innervation to neurons throughout the cerebral cortex, including neurons in the PC/RS cortex, have m2 receptor protein localized to their cell bodies. In addition, the Applicants have localized m2 receptor protein to axon terminals in the PC/RS cortex and have found m3 receptor protein in the cell bodies and dendrites of pyramidal neurons in the PC/RS cortex.

Although localization of m2 receptor protein to the cell body of cholinergic neurons could be interpreted as evidence that these neurons have m2 receptors on their cell body surface the Applicants' finding that m2 receptors are also present in PC/RS cortical axon terminals indicates that these m2 receptors are autoreceptors that are synthesized in the cell body of cholinergic neurons and then are transported through the axon fiber out to its terminal tip in the PC/RS cortex where the axon terminal forms a synaptic contact with an m3 receptor on the surface of the PC/RS pyramidal neuron (neuron 100 in FIG. 1). At this synapse, the cholinergic axon terminal releases (secretes) acetylcholine onto the m3 receptor. The m2 autoreceptor on the axon terminal functions to regulate (inhibit) the rate at which acetylcholine is released upon the m3 receptor.

The Applicants' new findings pertaining to m2 muscarinic autoreceptors provides new insight into the basis for the clinical benefits conferred by tacrine. Like all cholinesterase inhibitors, tacrine increases the duration of action of ACh at muscarinic receptors. If it increased the duration of action of ACh at m2 autoreceptors that inhibit the release of ACh at m3 receptors on PC/RS neurons this will decrease the amount of ACh released at the m3 receptors and decrease the activity of these receptors, which is the type of action that the Applicants' NR/hypo model predicts would be beneficial. Since tacrine is moderately beneficial in Alzheimer's disease, this suggests that the Applicants' assertions may be correct, and that those who are pursuing drug development programs aimed at increasing the activity of m1 or m3 receptors may be operating on a false premise.

Example 4

Evidence form Human Studies which Corroborates Hyperactivity at Muscarinic Receptors as a Mechanism Contributing to Neurodegeneration in the Early Stages of Alzheimer's Disease A. Evidence from the Applicants' laboratories The Applicants are engaged in research at the Washington University School of Medicine, in St. Louis. At this medical school, an Alzheimer's Disease Research Center (ADRC) maintains a brain bank, containing preserved brains and brain tissue from many deceased Alzheimer patients. These brains and tissue sections have been separated into categories based on the clinical stage of illness at the time when the patient died. In a small group of patients, death occurred very early in the disease.

In a major study that the Applicants have undertaken in collaboration with Daniel McKeel, MD, Chief Pathologist and Director of the ADRC Brain Bank, an initial observation has been made that in patients who died in the early stages of the disease, basal forebrain cholinergic neurons appear to be well preserved. By contrast, in patients who died in the very late stages of Alzheimer's disease, cholinergic neuronal loss is striking. These findings have not previously been published or publicly communicated. The Applicants and Dr. McKeel intend to expand the study to include a larger number of Alzheimer brains in both early and late stages of the disease, and will report the findings in a scientific journal when this goal is achieved.

On the basis of these initial findings, it appears that in the early stages of Alzheimer's disease, the cholinergic muscarinic transmitter system is intact and viable, contrary to the assumptions of most Alzheimer researchers, who believe or assume that it is hypoactive or even defunct. These findings strongly support the Applicants' NR/hypo assertions, which hold that (1) the cholinergic system is intact early in Alzheimer's disease; (2) both the cholinergic system and non-NMDA glutamate system are hyperactive, early in Alzheimer's disease; and (3) this hyperactivity wreaks havoc with many neurons throughout the brain. The Applicants assert that it is only in the late stages of the disease, after cholinergic neurons have contributed to the death of many other neurons, that the cholinergic neurons degenerate, probably from exhaustion due to chronic hyperactivity.

B. Evidence from a second independent laboratory

In recent years, new methods have been developed for non-invasively imaging the brains of Alzheimer patients who are still alive. One such method, magnetic resonance spectroscopy, provides for the use of tracer molecules that reveal the status of certain neuronal systems and neurochemical processes in the living brain. For example, it is possible to evaluate the status of the cholinergic neurons, using choline as a tracer, and to evaluate the status of other neurons using n-acetyl-aspartyl-glutamate as tracer.

In a recent study using these methods, Ross et al 1993 reported that early in the course of Alzheimer's disease, cholinergic neurons appeared to be intact, while substantial evidence for loss of other neurons was discernible. In addition, Ross et al noted that early in Alzheimer's disease, the phosphoinositide second messenger system that is coupled to m3 cholinergic receptors appeared to be accumulating excessive amounts of certain metabolites. Consistent with the Applicants' assertions herein, this suggests that early in Alzheimer's disease, the cholinergic system is not only intact and active, but that it may be overly active.

Example 5

Evidence that NMDA Receptor Hyperactivity can Damage the NMDA Receptor System and Render it Hypofunctional The focus of attention in the excitotoxicology research field has been on the phenomenon of NMDA receptor hyperactivity, and on the ability of such hyperactivity to cause excitotoxic neuronal degeneration in various neurological disorders. The possibility that excessive activation of NMDA receptors will result in damage to the NMDA receptor system, and cause this system to become hypofunctional, and that the subsequent state of NMDA receptor hypofunction might act as a disease mechanism, is a concept that is new to excitotoxicologists, and goes beyond what they have been traditionally taught. Thus, the status of this concept at the present time is that it is being introduced by the Applicants, and it has not yet been accepted by the majority of neurologists.

The Applicants' assertion in relation to Alzheimer's disease is that the NMDA receptor hyperactivity, which initiates the process, arises spontaneously, by a process which (in many patients) involves beta amyloid protein, which causes NMDA receptors to become hypersensitized. However, in the following paragraph, experiments conducted by the Applicants pertaining to an entirely different neural system in the brain (the hypothalamic-pituitary neuroendocrine regulatory system) illustrate that when the NMDA receptor hyperactivity is triggered experimentally, the end result is the same, i.e., excitotoxic damage to the NMDA receptor system is caused by over-excitation of the NMDA receptors; this damage renders the NMDA receptor system hypofunctional; and, the resulting NR/hypo condition then becomes a disease mechanism, which can cause various symptoms and degenerative changes to occur.

The Applicants have shown that administration of NMDA subcutaneously or intravenously to rodents causes neurons in the hypothalamus (a brain region at the base of the brain immediately above the pituitary gland) to send a message to the pituitary gland, causing the pituitary gland to secrete into the blood certain reproductive hormones such as luteinizing hormone (LH). The explanation for this is that normally, neurons in the hypothalamus that have NMDA receptors on their surface are activated by the excitatory transmitter, glutamate, which causes them to send a message to the pituitary resulting in pituitary release of LH. When NMDA is administered, it enters the hypothalamus and mimics glutamate by acting at the same NMDA receptors that glutamate would activate. This triggers the same sequence of events that glutamate would normally trigger. The action of glutamate at these NMDA receptors represents a physiological mechanism by which glutamate normally regulates the amount of reproductive hormones (e.g., LH) that circulate in the blood. For a detailed review describing this neuroendocrine regulatory system, see Olney and Price 1978.

The Applicants have found that they can permanently damage and inactivate this reproductive regulatory system, by administering a high dose of NMDA or glutamate to rats. These excitotoxic molecules (NMDA or glutamate) enter the hypothalamus and hyperactivate NMDA receptors so vigorously and continuously that it destroys the NMDA receptor system, and leaves it permanently unresponsive to subsequent stimulation, either by exogenously administered NMDA, or by endogenous glutamate. This is easily confirmed by the fact that after the damage has been done, administration of NMDA does not cause an increase in blood levels of LH.

Confirmation that the system is no longer responsive to endogenous glutamate, after it has suffered a chemical assault by NMDA leading to overstimulation of the NMDA receptors, is found in the fact that circulating levels of LH are drastically reduced. Affected animals develop a neuroendocrine deficiency syndrome, which leads to symptoms such as obesity, sterility, and ongoing degeneration of their reproductive organs.

Thus, by an experimental manipulation causing hyperactivation of NMDA receptors, an NMDA receptor system was damaged and the physiological mechanism by which this system normally regulates reproductive function was rendered hypofunctional and incompetent (an NR/hypo state). The NR/hypo condition then became a disease mechanism which caused the animals to develop obesity, sterility, and ongoing degeneration of reproductive organs as the symptomatic manifestations of this experimentally-induced disease of the neuroendocrine regulatory system.

This example of an experimentally induced disease state is offered as an analogy which models and demonstrates what can happen spontaneously in an Alzheimer brain, when beta amyloid accumulation renders NMDA receptors hypersensitive to glutamate. The hypersensitivity causes damage to the NMDA receptor system, which results in an NR/hypo condition. This condition then begins to function as a disease mechanism, which causes widespread neurodegeneration and cognitive deterioration.

Example 6

Evidence for a Specific Mechanism that may Cause Pathological Induction of NR/HYPO in an Alzheimer Brain The experiment described in Example 5 shows that by a controlled manipulation that causes hyperactivation of NMDA receptors in a certain brain circuit, it is possible to convert that circuit from a healthy physiologically functional system to a system compromised by NMDA receptor hypofunction, which can subsequently cause the system to function pathologically and give rise to symptoms of disease. The Applicants assert herein that an analogous phenomenon occurs in the early stages of Alzheimer's disease, but that the initial mechanism triggering the NMDA receptor hyperactivity is one that is activated spontaneously, due to a genetic predisposition of the Alzheimer brain to accumulate beta amyloid in a diffuse distribution such that it comes in contact with certain NMDA receptors in the NMDA receptor circuitry depicted in FIG. 1.

In the present example, specific lines of evidence reported by several laboratories are cited to show that (1) the Alzheimer brain is subject to genetic predispositions to accumulate beta amyloid; and, (2) when beta amyloid comes in contact with NMDA receptors, it makes the NMDA receptors hypersensitive to excitotoxic stimulation. This makes the NMDA receptor system vulnerable to degeneration, which then renders the system hypofunctional.

In certain rare forms of Alzheimer's disease, genetic defects have been found involving a genetic locus that regulates the processing of amyloid precursor protein (Selkoe et al 1994). Patients having this type of defect have an early onset of Alzheimer's disease which is associated with deposition in the brain of large amounts of beta amyloid, the protein that is responsible for the formation of amyloid plaques.

In the more common sporadic forms of Alzheimer's disease it has been found (Roses 1991) that individuals who have a certain apolipoprotein allele (E4) have an increased chance of developing Alzheimer's disease and a tendency to develop Alzheimer's disease earlier in life. It has also been reported (Schmechel et al 1993) that patients with the E4 allele have an increased tendency to secrete and deposit beta amyloid in the brain.

Other researchers have shown in in vitro experiments that when beta amyloid is added to the incubation medium surrounding cultured neurons, it causes the NMDA receptors on these neurons to become hypersensitive to the excitotoxic action of glutamate, so that concentrations of glutamate that would otherwise be innocuous become sufficient to overexcite and destroy these neurons and their NMDA receptors (Koh et al 1990).

Thus, it appears that Alzheimer patients may be subject to any of several possible genetic defects that leave them predisposed to accumulate abnormal amounts of beta amyloid in brain tissue, where it interacts with NMDA receptors to cause the receptors to become pathologically hyper-irritable and prone to excitotoxic injury. This type of injury may destroy the membrane sites where the NMDA receptors are located, or it may destroy entire NMDA receptor-bearing neurons, with their receptor. In either case, loss of NMDA receptors occurs, and the NMDA receptor system is thereby rendered hypofunctional.

Although it is known to other researchers in the Alzheimer's disease field that beta amyloid can cause NMDA receptor hyperactivity, it appears that no other researchers in this field have drawn the same conclusions as the Applicants. Those in the genetics school have adhered to the general belief that the neurodegenerative aspects of Alzheimer's disease can be explained in terms of beta amyloid accumulating in the vicinity of target neurons and exerting a toxic influence on these neurons, causing them to develop NFT and undergo progressive degeneration. A major problem they have not managed to resolve is the fact that the distribution of beta amyloid deposits in the Alzheimer brain does not correspond with the distribution of degenerating NFT-bearing neurons. This lack of correlation suggests that if beta amyloid triggers the neurodegeneration it must do so by an indirect or remote mechanism that does not involve direct contact between beta amyloid and the degenerating neurons.

Although members of the Genetics School have not described or apparently conceived of any remote mechanism by which beta amyloid could be instrumental in causing neuronal degeneration in Alzheimer's disease, this is precisely the type of mechanism that the Applicants are now describing. The Applicants assert that beta amyloid accumulates not in direct contact with the target neuron (neuron 100 in FIG. 1), but in the vicinity of the NMDA receptors on other neurons (e.g. neurons 20–50 in FIG. 1), which are distributed in various remote brain regions in a pattern that does not correspond with the distribution of the PC/RS target neuron 100. The interaction of beta amyloid with NMDA receptors in these various other brain regions initiates a complex and highly indirect neurotoxic process that is conveyed via long fiber tracts and multiple synaptic connections from the site of beta amyloid/NMDA receptor interaction to the PC/RS target neuron 100.

Thus, although members of the Genetics School are currently either unaware of or apparently uninterested in the Applicants' model, it is a model that holds promise of removing a major stumbling block that has impeded the progress of these researchers for several decades. Over the past decade, and during the last year while the Applicants have developed their conceptual model, the Genetics School has become increasingly preoccupied with beta amyloid, and with the possibility that it can act as an autonomous factor which is capable, by itself, of destroying neurons. However, they have shown no apparent inclination to think in terms of beta amyloid acting through NMDA receptors to hyperactivate and burn out these receptors, and thereby unleash an NR/hypo mechanism seemingly unrelated to beta amyloid which can cause widespread degeneration of neurons.

On the other side of the fence, those in the excitotoxicology school of Alzheimer research have considered ways in which defects in energy metabolism, or defects involving beta amyloid, can increase the sensitivity of NMDA receptors to excitotoxic stimulation. However, this has brought them to an impasse, in which they postulate that NMDA receptors would become hyperactive, which seemingly contradicts evidence that the NMDA receptor system in the aging brain is hypoactive.

Thus, at the present time, no other Alzheimer researchers have reported or offered the correlations and sequential damage processes described herein (starting with beta amyloid abnormalities, leading to NMDA receptor hyperactivity, leading to NMDA receptor damage, leading to NMDA receptor hypofunction, leading to a loss of glutamate-driven inhibitory control, leading to widespread neurodegeneration). These correlations appear to offer a logical sequential mechanism that incorporates evidence from the genetics school, the excitotoxicity school, and the Applicants' own research, which apparently can explain the complete sequence and pathology of Alzheimer's disease.

Example 7

Evidence that a Substantial Degree of NR/HYPO Exists in the "Normal" Aging Brain In the past 5 years, at least 4 different research groups who are adherents of the excitotoxic hypothesis (i.e., that excessive activation of NMDA receptors causes neuronal degeneration in Alzheimer's disease), have conducted studies to evaluate the status of the NMDA receptor system in the aging brains of rodents and monkeys. These studies were motivated by the belief that the NMDA receptor system might show signs of increasing hyperactivity as a function of aging. If researchers could prove that this belief holds true, it would support their hypothesis that the widespread degeneration of neurons that occurs in Alzheimer's disease is mediated by straightforward excitotoxic hyperactivation of NMDA receptors.

However, in each of those studies (Tamaru et al 1991; Wenk et al 1991; Gonzales et al 1991; Magnusson and Cotman 1993), the authors found evidence for a progressive decrease in the activity and functional capacity of the NMDA receptor system, as a function of increasing age.

Since hypofunction of the NMDA receptor system in old age did not seem to support their NMDA receptor hyperactivity hypothesis, those authors reported their data as generally negative findings, which they could not relate to Alzheimer's disease. None of those published reports suggested that hypofunction of the NMDA receptor system could be a mechanism operative in an Alzheimer brain to mediate the pathological manifestations of Alzheimer's disease, such as neurofibrillary tangles, loss of synaptic complexes, and certain other patterns of neuronal degeneration.

If, in a normal aging brain, there is a moderately severe degree of NMDA receptor hypofunction, merely as a result of aging (as the above-cited studies document), then in a "normal" aging brain, the stage may be set for widespread Alzheimer-like neurodegeneration to occur, if an auxiliary disease-linked mechanism somehow augments or accelerates the aging mechanism by which NMDA receptor hypofunction is already beginning to occur.

Example 6, above, cites evidence for a genetic predisposition which causes Alzheimer patients to accumulate beta amyloid in the brain, which can cause NMDA receptor hyperactivity, leading to receptor damage and subsequent hypoactivity. Thus, based on several lines of evidence they have assimilated, the Applicants assert that an age-linked NR/hypo mechanism combines with an additional beta-amyloid pathology, and these two mechanisms, acting in concert, trigger widespread corticolimbic neurodegeneration.

Example 8

Screening Assays to Evaluate the Potency of NMDA Antagonists (Chick Retina Assays)

All of the candidate NMDA antagonist drugs tested by the Applicants in these assays had previously been reported as NMDA antagonists, by other researchers. Accordingly, the results from these assays should be regarded as confirmatory, rather than as new discoveries.

These experiments were performed using segments of chick embryo retina. This is a widely used model for studying the production and prevention of excitotoxic phenomena, since it is a simple and inexpensive preparation, and since chick tissue provides a better model of adult mammalian neurons than embryonic or juvenile mammalian tissue. All of the glutamate receptors that mediate excitotoxic phenomena are present in chick retinas, and are sensitive to excitotoxic stimulation. By contrast, in embryonic or juvenile mammalian tissue, various glutamate receptors are not fully matured and are not responsive in the same ways that occur in adult mammalian tissue.

In these tests, NMDA is introduced into the incubation medium in a concentration (40 $\mu$M) sufficient to produce a fully developed excitotoxic lesion within 30 min, displaying acute degeneration and necrosis of the majority of neurons in the inner layers of the retina. The control retinas are incubated with NMDA alone, and experimental retinas are incubated with NMDA plus a test compound that is being evaluated for NMDA antagonist properties. The test compound is added to the incubation in a wide range of concentrations, to determine whether (and at what concentration) it is able to totally prevent the acute degenerative reaction induced in the chick retina by NMDA. All agents that prevent NMDA from hyperactivating NMDA receptors and thereby inducing an excitotoxic neurodegenerative reaction in the chick embryo retina are considered appropriate candidate drugs for preventing NMDA receptor hyperactivation and NMDA receptor burnout in the presymptomatic stages of Alzheimer's disease.

The concentration of the test compound required to prevent NMDA from inducing neuronal degeneration in the chick retina tissue is considered a measure of its expected potency for preventing NMDA receptor hyperactivation and NMDA receptor burnout in the presymptomatic stages of Alzheimer's disease.

As noted in the "Overview" section, the NMDA antagonists tested by the Applicants can be divided into four categories: (1) competitive NMDA antagonists, which act at the glutamate binding site; (2) non-competitive NMDA antagonists which act at the glycine binding site; (3) non-competitive "open channel" NMDA antagonists that act at the PCP binding site; and, (4) non-competitive NMDA antagonists that block NMDA receptors by action at the polyamine binding site.

Table 1 contains the results of those tests, expressed as the dosage of each agent that was required to effectively block all (or substantially all) of the toxic lesion formation in chick retina tissue exposed to a fixed quantity of NMDA. Because of the nature of these assays and the endpoints they generate, they do not lend themselves to calculating other values, such as $ED_{50}$ values or confidence limits which indicate 25% or 75% protection levels.

Example 9

In Vivo Assays to Quantify Toxic Side Effects Caused by NMDA Antagonist Drugs

Any drug that was confirmed by the Applicants as an effective NMDA antagonist (using the screening assay described in Example 8) was tested in a second assay to determine whether, and to what extent, it caused toxic side effects. In this second assay, adult female Sprague Dawley rats were injected intraperitoneally (ip) with various doses of the NMDA antagonist and were sacrificed four hours after treatment, for histopathological evaluation of the brain to determine whether a neurotoxic reaction had occurred. The neurotoxic reaction typically caused by NMDA antagonist drugs consists of acute vacuole formation in the majority of pyramidal neurons in layers III and IV of the posterior cingulate and retrosplenial (PC/RS) cortices.

Two of the drugs screened by the Applicants using this assay, eliprodil and ibogaine, did not cause this neurotoxic reaction. In addition, a quinoxaline called NBQX also did not cause vacuoles; it was more difficult to handle, because of certain pharmacokinetic properties, so it is described in Example 11, below.

Example 10

Evaluation of Eliprodil and Ibogaine

Eliprodil, which acts at the polyamine site on the NMDA receptor, was evaluated by the Applicants in the chick retina

TABLE 1

COMPARATIVE POTENCIES OF NMDA ANTAGONISTS

| NMDA ANTAGONIST (AND BINDING SITE) | POTENCY RATING ($\mu$M) |
|---|---|
| COMPETITIVE (Glutamate Binding Site) | |
| CGS 19755 | 5 |
| CPP | 10 |
| D-AP5 | 25 |
| NON-COMPETITIVE PCP Binding Site | |
| MK-801 | 0.3 |
| Phencyclidine | 1 |
| Tiletamine | 5 |
| Ketamine | 10 |
| Procyclidine | 15 |
| Ibogaine | 15 |
| Dextromethorphan | 25 |
| Polyamine Binding Site | |
| Eliprodil | 30 |
| Ifenprodil | 50 |
| Glycine Binding Site | |
| 7-CL-Kynurenic acid | 50 |
| CNQX | 200 |
| DNQX | 100 |
| NBQX | 100 |

Potency rating = minimum concentration required to provide total protection against neurotoxic effects of NMDA (40 $\mu$M) in chick embryo retinal tissue tests assay and found to have definite NMDA antagonist properties. Then it was introduced into the second screening assay at a wide range of doses from 1 to 100 mg/kg/ip. At the highest dose tested (100 mg/kg/ip), which was nearly a lethal dose, it did not cause a neurotoxic reaction in the PC/RS cortex.

It had previously been reported (Contreras et al 1990; also see Carter et al 1988 and 1989) that eliprodil has strong binding activity at sigma receptors, although it had not been reported whether eliprodil was an agonist or antagonist. It also had been discovered previously by the Applicants that blockade of sigma receptors can help suppress the toxic side effects of NMDA antagonists, as discussed above and as shown in FIGS. 1 and 2. Therefore, the Applicants suspected that eliprodil's absence of toxic side effects was probably due to a blocking activity at sigma receptors.

To evaluate this possibility, they tested a combination of eliprodil and SKF (+)10,047, a drug known to have selective agonizing activity at sigma receptors, in rats. They reasoned that if blockade of a sigma receptor was preventing eliprodil from displaying neurotoxic activity, administration of eliprodil with a sigma agonist would counteract and cancel out the sigma blocking activity, and would allow the neurotoxic potential of eliprodil's NMDA blocking activity to be expressed. This prediction was indeed borne out. A combination of SKF (+)10,047 together with eliprodil induced a vacuole reaction in PC/RS neurons, whereas neither SKF (+)10,047 by itself, nor eliprodil by itself, caused a vacuole reaction.

Ibogaine, an agent that acts at the PCP site in the NMDA receptor ion channel, was evaluated by the Applicants in the chick retina assay and found to have definite NMDA antagonist properties. Then it was introduced into the second screening assay at a wide range of doses from 1 to 100 mg/kg/ip. At the highest dose tested (100 mg/kg/ip) which was nearly a lethal dose, it did not cause a neurotoxic reaction in the PC/RS cortex.

For many years, it has been thought that the primary mechanism by which ibogaine exerts its effects in the brain involves interactions with serotonin (5HT) receptors. A recent study (Mash et al 1995) suggests that this may involve an indirect mechanism, in which a metabolite of ibogaine interacts with a serotonin transporter and thereby causes increased amounts of serotonin to accumulate at serotonin receptors. In addition, other recent studies reported that ibogaine has strong binding affinity at sigma -receptors (Mach et al 1995, Popik et al 1995, and test results gathered at about the same time by the Applicants). These studies on sigma receptors suggested to the Applicants that the absence of toxic side effects from ibogaine might be due to its interaction with sigma receptors, rather than (or possibly in addition to) serotonin receptors.

To test this possibility, the Applicants co-administered SKF (+)10,047, a selective sigma agonist as noted above, together with ibogaine. The combination caused a vacuole reaction in PC/RS neurons, whereas neither SKF (+)10,047 nor ibogaine by itself caused vacuoles. This suggests that ibogaine, like eliprodil, has a built-in safener action mediated through a sigma receptor, and it may also have an additional safening activity by acting through serotonin receptors.

As noted above, ibogaine has two closely related analogs (ibogamine and tabernanthin) which have been isolated from Apocynaceae plants. These agents are believed to have neurological activities that are very similar to ibogaine, and they (and their analogs) are regarded as having the same neuroprotective potential in Alzheimer's disease as ibogaine.

Example 11

Evaluation of NBQX as a Safening Agent

During a series of tests carried out in 1994 and 1995, the Applicants discovered that fully developed toxic side effects in pyramidal neurons could be induced by simultaneously administering three different types of elective agonist drugs. These drugs had to simultaneously stimulate three separate receptor pathways (muscarinic, sigma, and non-NMDA glutamate) on PC/RS neurons in order to induce the same type of neurotoxic response that could be generated by NMDA antagonist drugs such as PCP or MK-803. After these results were observed, it was realized that blockade of non-NMDA glutamate receptors might be sufficient to prevent this type of neurotoxic reaction.

To test that hypothesis, the Applicants injected NBQX (15 mg/kg) intraperitoneally (ip) at the same time as MK-801 (0.5 mg/kg, ip or sc). Because of the problems of apparent ejection of NBQX by brain tissue, as mentioned above, an additional bolus of NBQX (15 mg/kg) was injected every 30 minutes, for a total of 4 injections for each animal. The rats were sacrificed four hours after the treatment began, and brain tissue from the PC/RS region was histologically evaluated, by previously described methods (Olney et al 1991) using double-blinded techniques. The number of vacuolated PC/RS neurons were counted on each side of the brain at a rostrocaudal level immediately posterior to where the corpus callosum ceases decussating across the midline (approximately 5.6 mm caudal to Bregma; see Paxinos & Watson, *The Rat Brain in Stereotaxic Coordinates*, 2nd ed., 1986). In previous tests (Farber et al 1993), the Applicants had found that the toxic reaction approaches maximal severity at this level and does not vary much in severity from one animal to another.

The results showed that all animals (n=6) receiving only MK-801 had a severe vacuole reaction in the PC/RS cortex (199.3±8.1 SEM vacuolated neurons per microscopic section), whereas animals that received both MK-801 and NBQX had a significantly reduced number of vacuolated neurons (52±22.4 SEM vacuolated neurons per microscopic section). However, there was a wide range of variation among the experimental animals, with some rats having no vacuolated neurons while others had a relatively severe reaction. This high level of variance was interpreted as a reflection of the erratic pharmacokinetics of NBQX in brain tissue.

To try to avoid that problem, a subsequent set of tests was carried out in which NBQX was microinjected directly into the PC/RS cortex, at one of two doses, either 0.025 or 0.25 nmols. In these tests, all animals received MK-801, injected intraperitoneally; this caused the MK-801 to affect both sides of the brain. One side of the brain was injected with NBQX, which protected only that side, allowing the other side of the brain to provide control data. The vacuole responses in the unprotected (contralateral) side of the brains were severe (average 212±7.9 SEM vacuolated neurons per microscopic section). By contrast, the protected (ipsilateral) side of the brain showed a marked reduction in the number of vacuolated neurons; the lower dosage of NBQX reduced vacuoles by about 20%, while the higher dosage reduced vacuoles by about 80%.

Example 12

Assays to Evaluate other Safening Agents

Adult female Sprague Dawley rats were injected intraperitoneally (ip) with various doses of a test compound (i.e., a potential "safener" drug which is a candidate for treating Alzheimer's disease). At the same time, test animals also received a subcutaneous (sc) injection of MK-801 (0.5 mg/kg), a powerful NMDA antagonist. This dose of MK-801 had been shown to consistently induce, in all treated rats, a fully developed neurotoxic reaction consisting of acute vacuole formation in the majority of pyramidal neurons in layers III and IV of the posterior cingulate and retrosplenial (PC/RS) cortices.

Control animals received the liquid which was used to dissolve the test agent, plus the same dosage of MK-801 (0.5 mg/kg sc). For each test agent, at least 5 dosages of the candidate safener agent were tested, and at least 4 rats were used in each dosage group.

The rats were sacrificed four hours after treatment, for histopathological evaluation. The number of vacuolated PC/RS neurons were counted on each side of the brain, at a rostrocaudal level immediately posterior to where the corpus callosum ceases decussating across the midline (approximately 5.6 mm caudal to bregma). The Applicants had previously found that the vacuole reaction approaches maximal severity at this level, and shows very little variability between different animals.

Percentage reductions in the neurotoxic side effects caused by the MK-801 were calculated by dividing the mean number of vacuolated neurons in a given treatment group, by the mean number of vacuolated neurons in control animals that were treated with MK-801 but not the safener agent. The result was subtracted from one and multiplied by 100, to calculate a percentage. Linear regression analysis was used to determine an $ED_{50}$ (i.e., the effective dosage of a given compound that reduced the mean number of vacuolated neurons to 50% of the value in control animals).

The results of these assays are provided in Table 2. The confidence limits, in the right column, were the safener dosages that reduced vacuoles by 25% and 75%.

The following is a listing of drugs that have been shown to block the toxic side effects of MK-801. Not all of these drugs would be suitable for long-term chronic administration to treat Alzheimer's disease, because of potential side effects; however, a prescribing physician who is familiar with these drugs (and their side effects) can determine which particular drugs are best suited for any individual Alzheimer patient. Accordingly, having a fairly broad array of candidate drugs which have been discovered and identified as having the crucial neuroprotective property (i.e., the ability to protect against NR/hypo-mediated neuronal damage, as shown by the safener assay described above) is quite valuable, and offers physicians and patients a useful range of candidate treatments.

(1) Anticholinergic drugs which block the muscarinic class of cholinergic receptors. Such drugs include scopolamine, atropine, benztropine, trihexyphenidyl, biperiden, procyclidine, benactyzine, and diphenhydramine. See

TABLE 2

POTENCY RANKINGS OF VARIOUS SAFENER DRUGS

| SAFENER DRUG | ED50 (mg/kg, ip) | Confidence Limits (25% and 75%) |
|---|---|---|
| Group 1 (Anticholinergics) | | |
| Scopolamine | 0.13 | (0.08–0.18) |
| Benztropine | 1.29 | (0.92–1.65) |
| Trihexyphenidyl | 2.14 | (1.26–3.57) |
| Group 2 (Atypical Antipsychotics) | | |
| Olanzapine | 0.6 | (0.2–1.9) |
| Fluperlapine | 2.4 | (1.3–4.5) |
| Clozapine | 2.8 | (1.5–5.1) |
| Group 3 (GABA Facilitators) | | |
| Diazepam | 1.0 | * |
| Pentobarbital | 13.07 | (9.48–16.65) |
| Secobarbital | 15.28 | (10.91–19.66) |
| Group 4 (Sigma Antagonists) | | |
| Haloperidiol | 5.1 | (2.4–10.9) |
| Rimcazole | 17.8 | (8.9–35.6) |
| Thioridazine | 55.3 | (25.0–122.2) |
| Group 5 (Alpha2-adrenergic Agonists) | | |
| Clonidine | 0.044 | (0.0088–0.22) |
| Guanabenz | 0.21 | (0.13–0.33) |

TABLE 2-continued

POTENCY RANKINGS OF VARIOUS SAFENER DRUGS

|  | SAFENER DRUG | ED50 (mg/kg, ip) | Confidence Limits (25% and 75%) |
|---|---|---|---|
|  | Lofexidine | 0.38 | (0.071–2.1) |
|  | p-Iodoclonidine | 1.3 | (0.29–5.8) |
| Group 6 | (Non-NMDA Glu Antagonists) | | |
|  | NBQX | | See Example 11 |
| Group 7 | (5HT2A Agonists) | | |
|  | Lisuride | 0.17 | (0.03–0.85) |
|  | DOB | 0.36 | (0.17–0.79) |
|  | DOI | 1.05 | (0.41–2.68) |

Olney et al 1991 and U.S. Pat. No. 5,034,400 (Olney 1991) for more information on these drugs.

(2) Certain drugs known as atypical antipsychotic agents, including clozapine, olanzapine and fluperlapine (Farber et al 1996). These drugs bind with variable affinity to several types of receptors, including those for the dopamine, serotonin and norepinephrine transmitter systems. In addition, they also bind to and act as antagonists at muscarinic cholinergic receptors. Therefore, for purposes of understanding the mechanism by which these drugs protect against NR/hypo neurodegenerative effects, it seems likely that their efficacy can be attributed at least in part to their ability to block muscarinic cholinergic receptors.

(3) Drugs which can increase activity at gamma-aminobutyric acid (GABA) receptors. Such drugs fall into two functional categories. Some, such as benzodiazepines (including diazepam, or VALIUM) increase the effects of naturally-occurring GABA. Others, such as certain barbiturates (including secobarbital and pentobarbital) act as "direct GABA agonists" because they can act directly at GABA-$_A$ receptors to open the chloride ion channel regardless of whether naturally-occurring GABA is present. In addition, some drugs that act at GABA receptors may have both types of activity (direct and indirect).

(4) Drugs that can bind to a class of receptors called sigma receptors (Farber et al 1993). These receptors are blocked by di(2-tolyl)guanidine and rimcazole, which are selective for sigma receptors, as well as other drugs such as haloperidol, thioridazine and loxapine, which interact with dopamine receptors as well as sigma receptors.

(5) Drugs that bind to a class of receptor called the alpha-2 adrenergic receptor and act as agonists at this receptor (Farber et al 1995). Drugs in this class include clonidine, guanabenz, p-iodoclonidine, xylazine, and lofexidine. Guanfacine was not tested by the Applicants; however, because of reported similarities between it and other alpha-2 adrenergics such as guanabenz, it is expected to provide similar protection.

(6) Drugs that act as antagonists at the two "non-NMDA" types of glutamate receptors (i.e., kainic acid receptors, and AMPA receptors). Such drugs include NBQX, LY 293558, LY 300164, GYKI 52466, and GYKI 53655.

(7) Drugs that act as agonists at a specific type of serotonin receptor, designated as the 5HT-2A receptor, have also been recently discovered by the Applicants to block the toxic side effects of NMDA antagonists. Drugs which agonize both 5HT-2A receptors and 5HT-2C receptors are usually hallucinogenic, and therefore are not good candidates for treating Alzheimer's disease, even though they are effective in blocking MK-801 toxicity. Drugs that agonize 5HT-2A receptors but not 5HT-2C receptors, such as lisuride, are better candidates for treating Alzheimer's disease, because they can block MK-801 toxicity without causing hallucinations.

Thus, there has been described a new model for understanding, and a new method for treating, Alzheimer's disease. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Albin, R. L. and Greenamayre, J. T., "Alternative excitotoxic hypothesis," Neurology 42: 733–738 (1992)

Beal, M. F., "Does impairment of energy metabolism result in excitotoxic neuronal death in neurodegenerative illnesses?" Ann. Neurol. 31: 119–130 (1992).

Boast, C. A., "Neuroprotection after brain ischemia: role of competitive NMDA antagonists," Neurology and Neurobiology 46: 691–698 (1988)

Bolden, C., et al, "Antagonism by antimuscarinic and neuroleptic compounds at the five cloned human muscarinic cholinergic receptors expressed in Chinese hamster ovary cells," J Pharm and Exp Ther 260: 576–580 (1992)

Braak, H. and Braak, E., "Neuropathological staging of Alzheimer-related changes," Acta Neuropathol 82: 239–259 (1991).

Brun, A. and Englund E., "Regional pattern of degeneration in Alzheimer's disease: neuronal loss and histopathological grading," Histopathology 5: 549–564 (1981)

Carter, C., et al, "Ifenprodil and SL 82.0715 as cerebral anti-ischemic agents. II. Evidence for NMDA receptor antagonist properties," J Pharmacol Exptl Ther 247: 1222–1232 (1988)

Checler, F., "Processing of the beta-amyloid precursor protein and its regulation in Alzheimer's disease," J Neurochem 65: 1431–44 (1995)

Choi, D. W., "Glutamate neurotoxicity and diseases of the nervous system," Neuron 1: 623–634 (1988)

Choi, D. W., "Excitotoxic cell death," J Neurobiol 23: 1261–1276 (1992)

Contreras, P. C. et al, "Ifenprodil and SL-82.0715 potently inhibit binding of $^3$H(+)-3-PPP to sigma binding sites in rat brain," Neurosci. Letters 115: 190–195 (1990)

Corso, T. D., et al, "Neuron necrotizing properties of phencyclidine," Soc Neurosci Abstr 20: 1531 (1994)

Ellison, G., "Competitive and non-competitive NMDA antagonists induce similar limbic degeneration," NeuroReport 5: 2688–2692 (1994)

Ellison, G., "The NMDA antagonists phencyclidine, ketamine and dizocilpine as both behavioral and anatomical models of the dementias," Brain Res. Rev. 20: 250–267 (1995)

Fagg, G. E., et al, "CGP 37849 and CGP 39551: novel competitive NMDA receptor antagonists with potent oral anticonvulsant activity," Prog Clin Biol Res 361: 421–7 (1990)

Farber, N. B., et al, "Alpha-2 adrenergic agonists prevent MK-801 neurotoxicity," Neuropsychopharmacology 12: 347–349 (1995)

Farber, N. B., et al, "Antipsychotic drugs block phencyclidine receptor-mediated neurotoxicity," *Biol Psychiatry* 34: 119–121 (1993)

Ferkany, J. W., et al, "Pharmacological profile of NPC 12626, a novel, competitive NMDA receptor antagonist," *J Pharmacol Exp Ther* 250: 100–109 (1989)

Ferkany, J. W., et al, "Pharmacological profile of NPC 17742 [2R,4R,5S-(2-amino-4,5-(1,2-cyclohexyl)-7-phosphonoheptanoic acid)], a potent, selective and competitive NMDA receptor antagonist," *J Pharmacol Exp Ther* 264: 256–64 (1993)

Fix, A. S., et al, "Light and electron microscopic evaluation of neuronal vacuolization and necrosis induced by the non-competitive NMDA antagonist MK-801 in the rat retrosplenial cortex," *Exp Neurol* 123: 204–215 (1993)

Gearing, M., et al, "Abeta-peptide length and apolipoprotein E genotype in Alzheimer's disease," *Ann Neurol* 39: 395–9 (1996)

Gonzales, R. A., et al, "NMDA-mediated responses decrease with age in Fischer 344 rat brain," *Neurobiology of Aging* 12: 219–225 (1991)

Grotta, J., "Safety and tolerability of the glutamate antagonist CGS 19755 in acute stroke patients," *Stroke* 25: 255 (1994)

Grotta, J., "Safety and tolerability of the glutamate antagonist CGS 19755 (Selfotel) in patients with acute ischemic stroke: Results of a Phase IIa randomized trial," *Stroke* 26: 602–605 (1995)

Hamos, J. E., et al, "Expression of heat shock proteins in Alzheimer's disease," *Neurol* 41: 345–350 (1991)

Hargreaves, R. J., et al, "competitive as well as uncompetitive NMDA receptor antagonists affect cortical neuronal morphology and cerebral glucose metabolism," *Neurochem Research* 18: 1263–1269 (1993)

Hendriks, L. and Van Broeckhoven, C., "A beta A4 amyloid precursor protein gene and Alzheimer's disease," *Eur J Biochem* 237: 6–15 (1996)

Henneberry, R. L., et al, "Neurotoxicity at the NMDA receptor in energy-compromised neurons: An hypothesis for cell death in aging and disease," *Ann NY Acad Sci* 568: 225–233 (1989)

Herrling, P. L. "D-CPPene (SDZ EAA 494), a competitive NMDA antagonist: Results from animal models and first results in humans," *Neuropsychopharmacology* 10, No 3S/Part 1: 591S (1994)

Insausti, R., et al, "The posterior cingulate cortex in man. Normal structure and changes in Alzheimer's disease," *Soc. Neurosci. Abstr.* 19: 357 (1993)

Ishimaru, M., et al, "Halothane prevents MK-801 neurotoxicity in the rat cingulate cortex," Neurosci Lett 193: 1–4 (1995)

Jagust, W. J., "Functional imaging patterns in Alzheimer's disease: Relationships to neurobiology," *Ann New York Acad Sci* 777: 30–36 (1996)

Javitt, D. C. and Zukin, S. R., "Recent Advances in the Phencyclidine Model of Schizophrenia," *Am J Psychiat* 148: 1301–1308 (1991)

Jevtovic-Todorovic, V., et al, "Isoflurane and propofol block neurotoxicity caused by MK-801 in the rat posterior cingulate/retrosplenial cortex," *J Cereb Blood Flow Metab, in press* (1996).

Jimerson, D. C., et al, "Preliminary trial of the noradrenergic agonist clonidine in psychiatric patients," *Biol. Psychiatry* 14: 45–57 (1980)

Keana, J. F., et al, "Synthesis and structure activity relationships of substituted 1,4-dihydroquinaxoline-2, 3-diones: Antagonists of NMDA receptor glycine sites and non-NMDA glutamate receptors," *J. Med. Chem.* 38: 4367–4379 (1995)

Kemp, J. A., et al, "Non-competitive antagonists of excitatory amino acid receptors," *TINS* 10: 294–299 (1987)

Koh, J., et al, "Beta-amyloid protein increases the vulnerability of cultured cortical neurons to excitotoxin damage," *Brain Res* 533: 315–320 (1990)

Kristensen, et al, "The NMDA-receptor antagonist CPP abolishes neurogenic 'wind-up pain' after intrathecal administration in humans," *Pain* 51: 249–253 (1992)

Krystal, J. H., et al, "Subanesthetic effects of the non-competitive NMDA antagonist, ketamine, in humans: Psychotomimetic, perceptual, cognitive, and neuroendocrine responses," *Arch. Gen. Psychiatry* 51: 199–214 (19394)

Luby, E. D., et al, "Model psychoses and schizophrenia," *Am J Psych* 119: 61–67 (1962)

Mach, R. H., et al, "Ibogaine possesses a selective affinity for sigma-2 receptors," *Life Sciences* 57: 57–62 (1995)

Magnusson, K. R. and Cotman, C. W., "Age-related changes in excitatory amino acid receptors in two mouse strains," *Neurobiology of Aging* 14: 197–206 (1993)

Mash, D. C., et al, "Identification of a primary metabolite of ibogaine that targets serotonin transporters and elevates serotonin," *Life Sciences* 57: 45–50 (1995)

Massieu, L., et al, "A comparative analysis of the neuroprotective properties of competitive and uncompetitive NMDA receptor antagonists in vivo," *Neuroscience* 55: 883–92 (1993)

Mayeux, R. and Schupf, N., "Apolipoprotein E and Alzheimer's disease: the implications of progress in molecular medicine," *Am J Public Health* 85: 1280–4 (1995)

Minoshima, S., et al, "Posterior cingulate cortex in Alzheimer's disease," *Lancet* 344: 895 (1994)

Morris, J. C., "The Clinical Dementia Rating (CDR): Current version and scoring rules," *Neurology* 43: 2412–2414 (1993)

Morris, J. C., et al, "Validation of clinical diagnostic criteria for Alzheimer's disease," *Ann Neurol* 24: 17–22 (1988)

Olney, J. W. and Price, M. T., "Excitotoxic amino acids as neuroendocrine probes," pp 239–263 in *Kainic Acid as a Tool in Neurobiology* (E. McGeer, et al, eds., Raven Press, blew York) 1978

Olney, J. W., et al, "Anti-Parkinsonian agents are phencyclidine agonists and N-methyl aspartate antagonists," *Eur. J. Pharmacol.* 142: 319–320 (1987)

Olney, J. W., "Glutamate," pp. 468–470 in *Encyclopedia of Neuroscience*, G. Adelman, ed. (Birkhauser, Boston, 1987)

Olney, J. W., "Excitotoxicity and NMDA receptors," *Drug Dev Res* 17: 299–319 (1989a)

Olney, J. W., et al, "Pathological changes induced in cerebrocortical neurons by phencyclidine and related drugs," *Science* 244: 1360–1362 (1989b)

Olney, J. W., "Excitotoxic amino acids and neuropsychiatric disorders," pp 47–71 in *Annual Review of Pharmacology and Toxicology, Volume* 30, R. George, et al, eds. (Annual Reviews, Inc, Palo Alto, Calif., 1990)

Olney, J. W., et al, "NMDA antagonist neurotoxicity: Mechanism and protection," *Science* 254: 1515–1518 (1991)

Olney, J. W. and Farber, N. B., "Efficacy of clozapine compared with other antipsychotics in preventing NMDA-antagonist neurotoxicity," *J Clin Psychiatry* 55(9) (*suppl. B*): 43–46 (1994)

Olney, J. W., "NMDA receptor hypofunction, excitotoxicity and Alzheimer's Disease," *Neurobiology of Aging* 16: 459–461 (1995)

Olney, J. W. and Farber, N. B., "Glutamate receptor dysfunction and schizophrenia," *Arch Gen Psych* 52: 998–1009 (1995)

Pericak-Vance, M. A., and Haines, J. L., "Genetic susceptibility to Alzheimer disease," *Trends Genet* 11: 504–8 (1995)

Polvikoski, T., et al, "Apolipoprotein E, dementia, and cortical deposition of beta-amyloid protein," *N Engl J Med* 333: 1242–7 (1995)

Popik, P., et al, "100 years of ibogaine: Neurochemical and pharmacological actions of a putative anti-addictive drug," *Pharmacological Reviews* 47: 235–253 (1995)

Price, J. L., et al, "The distribution of tangles, plaques and related immunohistochemical markers in healthy aging and Alzheimer's disease," *Neurobiology of Aging* 12: 295–312 (1991)

Reich, D. L. and Silvay, G., "Ketamine: an update on the first twenty years of clinical experience," *Can J Anaesth* 36: 186–197 (1989)

Roses, A. D., "Apolipoprotein E affects the rate of Alzheimer disease expression: B-amyloid burden is a secondary consequence dependent on APOE genotype and duration of disease," *J. Neuropath. Exp. Neurol.* 53: 429–437 (1991)

Rossor, M. N., et al, "Clinical and neuroimaging features of familial Alzheimer's disease," *Ann New York Acad Sci* 777: 49–56 (1996)

Schellenberg, G. D., "Progress in Alzheimer's, disease genetics," *Curr Opin Neurol* 8: 262–7 (1995)

Schmechel, D. E. A., "Increased amyloid B-peptide deposition in cerebral cortex as a consequence of apolipoprotein E genotype in late-onset Alzheimer disease," *Proc. Natl. Acad. Sci.* 90: 9649–9653 (1993)

Selkoe, D. G., "Alzheimer's disease: A central role for amyloid," *J Neuropath and Exp Neurol* 53: 438–447 (1994)

Smith, C. D., "Quantitative computed tomography and magnetic resonance imaging in aging and Alzheimer's disease," *J Neuroimaging* 6: 44–53 (1996)

Tamaru, M., et al, "Age-related decreases of the NMDA receptor complex in the rat cerebral cortex and hippocampus," *Brain Res* 542: 83–90 (1991)

Warner, D. S., et al, "In vio models of cerebral ischemia: effects of parenterally administered NMDA receptor glycine site antagonists," *J. Cerebral Blood flow and Metabolism* 15: 188–196 (1995)

Wenk, G. L., et al, "Loss of NMDA, but not GABA-A, binding in the brains of aged rats and monkeys," *Neurobiology of Aging* 12: 93–98 (1991)

We claim:

1. A method for treating presymptomatic Alzheimer's disease, comprising the following steps:

a. administering to a patient who does not yet display clinically detectable symptoms of Alzheimer's disease, but who has been diagnosed as having a presymptomatic disposition toward Alzheimer's disease, a drug regimen which includes an NMDA antagonist drug which penetrates mammalian blood-brain barriers and which has an inherent safener activity that prevents the NMDA antagonist drug from inflicting neurotoxic side effects inside the patient's brain, at a therapeutically effective dosage which prevents excessive excitation of NMDA receptors;

b. periodically evaluating the patient to determine whether the patient displays clinically detectable symptoms of Alzheimer's disease, so that administration of the NMDA antagonist drug can be terminated if clinically detectable symptoms of Alzheimer's disease are manifested by the patent.

2. The method of claim 1 wherein the NMDA antagonist drug which has an inherent safener activity is select from the group consisting of:

(a) ibogaine, ibogamine, tabernanthin, and salts, isomers, and analogs thereof which are therapeutically effective in suppressing activity at NMDA receptors without causing neurotoxic side effects in the patient's brain;

(b) eliprodil and salts, isomers, and analogs thereof which are therapeutically effective in suppressing activity at NMDA receptors without causing neurotoxic side effects in the patient's brain;

(c) procyclidine, trihexyphenydyl, and biperiden, and salts, isomers, and analogs thereof which are therapeutically effective in suppressing activity at NMDA receptors without causing neurotoxic side effects in the patient's brain; and, (d) quinoxalinediones which are therapeutically effective in suppressing activity at NMDA receptors without causing neurotoxic side effects in the patient's brain.

3. A method for treating patients suffering from an elevated risk of Alzheimer's disease, comprising the following steps:

a. administering to a patient who has been diagnosed as being at elevated risk of Alzheimer's disease, but who does not yet suffer from substantial damage to NMDA receptors on neurons inside the patient's central nervous system, a drug regimen which includes an NMDA antagonist drug which penetrates mammalian blood-brain barriers, and which has an inherent safener activity that prevents the NMDA antagonist drug from inflicting neurotoxic side effects inside the patient's brain, at a therapeutically effective dosage which prevents excessive excitation of NMDA receptors;

b. periodically evaluating the patient to determine whether the patient suffers from a condition of endogenous NMDA receptor hypofunctionality, so that administration of the NMDA antagonist drug can be terminated if a condition of endogenous NMDA receptor hypofunctionality is detected in the patent.

4. The method of claim 3 wherein the patient is periodically evaluated by means of a brain imaging technique selected from the group consisting of positron emission tomography, magnetic resonance imaging, and magnetic resonance spectroscopy.

5. The method of claim 3 wherein the patient is periodically evaluated by means of cognitive testing, using questions which evaluate perception, memory, and analytical abilities.

6. The method of claim 3 wherein the NMDA antagonist drug which has an inherent safener activity is selected from the group consisting of:
   (a) ibogaine, ibogamine, tabernanthin, and salts, isomers, and analogs thereof which are therapeutically effective in suppressing activity at NMDA receptors without causing neurotoxic side effects in the patient's brain;
   (b) eliprodil, and salts, isomers, and analogs thereof which are therapeutically effective in suppressing activity at NMDA receptors without causing neurotoxic side effects in the patient's brain;
   (c) procyclidine, trihexyphenydyl, and biperiden, and salts, isomers, and analogs thereof which are therapeutically effective in suppressing activity at NMDA receptors without causing neurotoxic side effects in the patient's brain; and,
   (d) quinoxalinediones which are therapeutically effective in suppressing activity at NMDA receptors without causing neurotoxic side effects in the patient's brain.

* * * * *